United States Patent [19]
Wong et al.

[11] Patent Number: 5,912,160
[45] Date of Patent: Jun. 15, 1999

[54] GAB1, GRB2 BINDING PROTEIN, AND COMPOSITIONS FOR MAKING AND METHODS OF USING THE SAME

[75] Inventors: Albert J. Wong; Marina Holgado-Madruga, both of Philadelphia, Pa.

[73] Assignee: Thomas Jefferson University, Philadelphia, Pa.

[21] Appl. No.: 08/701,240

[22] Filed: Aug. 22, 1996

Related U.S. Application Data

[60] Provisional application No. 60/002,641, Aug. 22, 1995.
[51] Int. Cl.$^6$ .................. C07K 14/705; C12N 15/12
[52] U.S. Cl. ............ 435/252.3; 435/69.1; 435/320.1; 530/350; 536/23.5; 536/24.3
[58] Field of Search ................... 435/69.1, 252.3, 435/320.1; 530/350; 536/23.5, 24.3

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |
| 5,108,921 | 4/1992 | Low et al. | 435/240.1 |
| 5,202,257 | 4/1993 | Heinemann et al. | 435/252.3 |

OTHER PUBLICATIONS

Bouwmeeste—et al., *Mech. of Develop.* 37:57–68, 1992.
Sunahara et al, *Nature* 350:614–619, Apr. 18, 1991.
Arad et al., "Use of reconstituted Sendai virus envelopes for fusion–mediated microinjection of double–stranded RNA: inhibition of protein synthesis in interferon–treated cells", *Biochem. Biophy. Acta.*, 1986, 859, 88–94.
Araki, E. et al., "Human Skeletal Muscle Insulin Receptor Substrate–1: Characterization of the cDNA, Gene and Chromosomal Localization", *Diabetes*, 1993, 42, 1041–1054.
Araki, E. et al., "Alternative pathway of insulin signalling in mice with targeted disruption of the IRS–1 gene", *Nature*, 1994, 372, 186–190.
Baltensperger, K. et al., "Binding of the Ras Activator Son of Sevenless to Insulin Receptor Substrate–1 Signaling Complexes", *Science*, 1993, 260, 1950–1952.
Capecchi, M.R., "Altering the Genome by Homologous Recombination", *Science*, 1989, 244, 1288–1292.
Chen, D. et al., "Insulin Receptor Substrate 1 Rescues Insulin Action in CHO Cells Expressing Mutant Insulin Receptors That Lack a Juxtamembrane NPXY Motif", *Molec. Cell Biol.*, 1995, 15(9), 4711–4717.
Crespo, P.J. et al., "Ras–dependent activation of MAP kinase pathway mediated by G–protein βγ subunits", *Nature*, 1994, 369, 418–420.
Downward, J., "The GRB2/Sem–5 adaptor protein", *FEBS Letters*, 1994, 338, 113–117.
Ekstrand, A.J. et al., "Functional characterization of an EGF receptor with a truncated extracellular domain expressed in glioblastomas with EGFR gene amplification", *Oncogene*, 1994, 9, 2313–2320.

Feng, S. et al., "Two Binding Orientations for Peptides to the Src SH3 Domain: Development of a General Model for SH3–Ligand Interactions", *Science*, 1994, 266, 1241–1247.
Gustafson, T.A. et al., "Phosphotyrosine–Dependent Interaction of SHC and Insulin Receptor Substrate 1 with the NPEY Motif of the Insulin Receptor via a Novel Non–SH2 Domain", *Mol. Cell. Bio.*, 1995, 15(5), 2500–2508.
Gout, I. et al., "The GTPase Dynamin Binds to and Is Activated by a Subset of SH3 Domains", *Cell*, 1993, 75, 25–36.
Holgado–Madruga, M. et al., "A Grb2–associated docking protein in EGF– and insulin–receptor signalling", *Nature*, 1996, 379, 560–564.
Jackman, J.K. et al., "Molecular Cloning of SLP–76, a 76–kDa Tyrosine Phosphoprotein Associated with Grb2 in T Cells", *J. Bio. Chem.*, 1995, 270(13), 7029–7032.
Lamphere, L. et al., "Activation of PI 3–kinase in 3T3–L1 adipocytes by assocation with insulin receptor substrate–1", *Am. J. Phsiol.*, 1994, 266, E486–494.
Lee, C.H. et al., "Nck associates with the SH2 domain–docking protein IRS–1 in insulin–stimulated cells", *Proc. Natl. Acad. U.S.A.*, 1993, 90, 11713–11717.
Li, P. et al., "Mice Deficient in IL–1β–Converting Enzyme Are Defective in Production of Mature IL–1β and Resistant to Endotoxic Shock", *Cell*, 1995, 80, 401–411.
Lowenstein, E.J. et al., "The SH2 and SH3 Domain–Containing Protein GRB2 Links Receptor Tyrosine Kinases to ras Signaling", *Cell*, 1992, 70, 431–442.
Moscatello, D.K. et al., "Frequent Expression of a Mutant Epidermal Growth Factor Receptor in Multiple Human Tumors", *Cancer Res.*, 1995, 55, 5536–5539.
Motto, D.G. et al., "In Vivo Association of Grb2 with pp116, a Substrate of the T Cell Antigen Receptor–activated Protein Tyrosine Kinase", *J. Bio. Chem.*, 1994, 269(34), 21608–21613.
Musacchio, A. et al., "The PH domain: a common piece in the structural patchwork of signalling proteins", *Trends. Biochem. Sci.*, 1993, 18, 343–348.

(List continued on next page.)

*Primary Examiner*—John Ulm
*Attorney, Agent, or Firm*—Woodcock Washburn Kurtz Mackiewicz & Norris LLP

[57] ABSTRACT

A substantially pure protein, Gab1, that binds to Grb2 is disclosed. Isolated nucleic acid molecules that encode Gab1 is disclosed. Pharmaceutical compositions comprising a pharmaceutically acceptable carrier in combination with nucleic acid molecules are disclosed. Fragments of nucleic acid molecules that encode Gab1 having at least 10 nucleotides and oligonucleotide molecule comprising a nucleotide sequence complimentary to a nucleotide sequence of at least 10 nucleotides are disclosed. Recombinant expression vectors that comprise the nucleic acid molecule that encode Gab1, and host cells that comprise such recombinant vectors are disclosed. Antibodies that bind to an epitope on Gab1 are disclosed. Methods of identifying inhibitors, activators and substrates of Gab1 are disclosed. Antisense compounds and methods of using the same are disclosed.

8 Claims, 9 Drawing Sheets

OTHER PUBLICATIONS

Myers, M.G. et al., "The New Elements of Insulin Signaling—Insulin Receptor Substrate–1 and Proteins with SH2 Domains", *Diabetes*, 1993, 42, 643–650.

Pruett, W. et al., "Association between GRB2/Sos and Insulin Receptor Substrate 1 is Not Sufficient for Activation of Extracellular Signal–Regulated Kinases by Interleukin–4: Implications for Ras Activation by Insulin", *Molec. Cell. Biol.*, 1995, 15(3), 1778–1785.

Reif, K. et al., "SH3 Domains of the Adapter Molecule Grb2 Complex with Two Proteins in T Cells: The Guanine Nucleotide Exchange Protein Sos and a 75–kDa Protein That is a Substrate for T Cell Antigen Receptor–activated Tyrosine Kinases", *J. Biol. Chem.*, 1994, 269(19), 14081–14087.

Ren, R. et al., "Abl protein–tyrosine kinase selects the Crk adapter as a substrate using SH3–binding sites", *Genes Dev.*, 1994, 8, 783–795.

Ron, D. et al., "pGSTag—A Versatile Bacterial Expression Plasmid for Enzymatic Labeling of Recombinant Proteins", *Biotech.*, 1992, 13(6), 866–869.

Sakai, R. et al., "A novel signalling molecule, p130, forms stable complexes in vivo with v–Crk and v–Src in a tyrosine phosphorylation–dependent manner", *EMBO J.*, 1994, 13(6), 3478–3756.

Schlaepfer, D.D. et al., "Integrin–mediated signal transduction linked to Ras pathway by GRB2 binding to focal adhesion kinase", *Nature*, 1994, 372, 786–791.

Skolnik, E.Y. et al., "The Function of GRB2 in Linking the Insulin Receptor to Ras Signaling Pathways", *Science*, 1993, 260, 1953–1955.

Soltoff, S.P. et al., "ErbB3 Is Involved in Activation of Phosphatidylinositol 3–Kinase by Epidermal Growth Factor", *Mol. Cell Biol.*, 1994, 14(6), 3550–3558.

Songyang, Z. et al., "Specific Motifs Recognized by the SH2 Domains of Csk, 3BP2, fps/fes, GRB–2, HCP, SHC, Syk, and Vav", *Mol. Cell. Biol.*, 1994, 14(4), 2777–2785.

Songyang, Z. et al., "SH2 Domains Recognize Specific Phosphopeptide Sequences", *Cell*, 1993, 72, 767–778.

Sun, X.J. et al., "Pleiotropic Insulin Signals Are Engaged by Multisite Phosphorylation of IRS–1", *Mol. Cell. Biol.*, 1993, 13(12), 7418–7428.

Sun, X.J. et al., "Structure of the insulin receptor substrate IRS–1 defines a unique signal transduction protein", *Nature*, 1991, 352, 73–77.

Sun, X.J. et al., "Role of IRS–2 in insulin and cytokine signalling", *Nature*, 1995, 377, 173–177.

Tamemoto, H. et al., "Insulin resistance and growth retardation in mice lacking insulin receptor substrate–1", *Nature*, 1994, 372, 182–186.

Tobe, K. et al., "Identification of a 190–kDa Protein as a Novel Substrate for the Insulin Receptor Kinase Functionally Similar to Insulin Receptor Substrate–1", *J. Biol. Chem.*, 1995, 270(11), 5698–5701.

Touhara, K. et al., "Binding of G Protein βγ–Subunits to Pleckstrin Homology Domains", *J. Biol. Chem.*, 1994, 269(14), 10217–10220.

Ullrich et al., "Insulin–like growth factor I receptor primary structure: comparison with insulin receptor suggests structural determinants that define functional specificity", *EMBO J.*, 1986, 5(10), 2503–2512.

Vuori, K. et al., "Association of Insulin Receptor Substrate–1 with Integrins", *Science*, 1994, 266, 1576–1578.

Wang, L.M. et al., "Common elements in interleukin 4 and insulin signaling pathways in factor–dependent hematopoietic cells", *Proc. Natl. Acad. Sci. U.S.A.*, 1993, 90, 4032–4036.

Wang, J. et al., "Direct Association of Grb2 with the p85 Subunit of Phosphatidylinositol 3–Kinase", *J. Biol. Chem.*, 1995, 270(21), 12774–12780.

White, M.F., "The IRS–1 signaling system", *Curr. Opin. Genet. And Dev.*, 1994, 4, 47–54.

Wong, A.J. et al., "The Molecular Biology and Molecular Genetics of Astrocytic Neoplasms", *Sem. Onc.*, 1994, 21(2), 139–148.

Yamauchi, K. et al., "Insulin Receptor Substrate–1 (IRS1) and Shc Compete for a Limited Pool of Grb2 in Mediating Insulin Downstream Signaling", *J. Biol. Chem.*, 1994, 269(49), 31107–31114.

Ye, Z.S. et al., "Binding of Vav to Grb2 through dimerization of Src homology 3 domains", *Proc. Natl. Acad. Sci. U.S.A.*, 1994, 91, 12629–12633.

Yu, H. et al., "Structural Basis for the Binding of Proline–Rich Peptides to SH3 Domains", *Cell*, 1994, 76, 933–945.

Hiller et al., "The WashU–Merck EST Project",Database GenBank–EST on IntelliGenetics, AN T86578, Mar. 17, 1995.

Holgado–Madruga et al., "Novel Effectors of Grb2 in Human Glial Tumors", *Proc. American Assoc. of Cancer Res.*, 1995, 36, 58, Abstract 343.

Humphery et al., "Anti–Synthetic Peptide Antibody Reacting at the Fusion Junction of Deletion–Mutant Epidermal Growth Factor Receptorsin Human Glioblastoma", *Proc. Natl. Acad. Sci.*, 1990, 87(11), 4207–4211.

Moscatello et al., "Altered Signal Transduction by a Mutant EGF Receptor From Human Tumors", *J. Cell. Biochem.*, 1994, Supp. 18B, 285, Abstract 1453.

PCT/U596/13842 Search Report (Nov. 29, 1996).

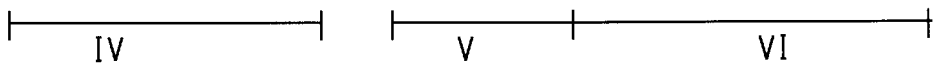
FIG.2

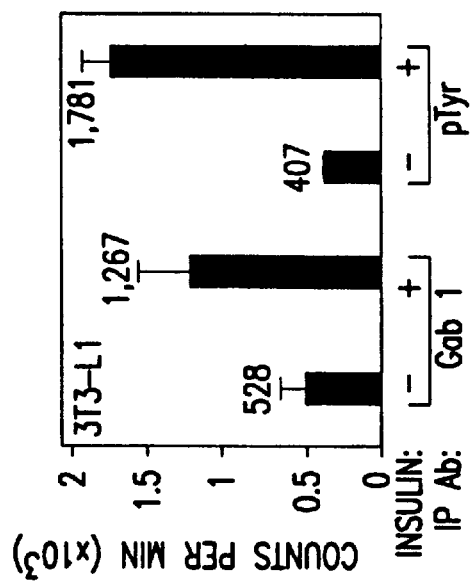
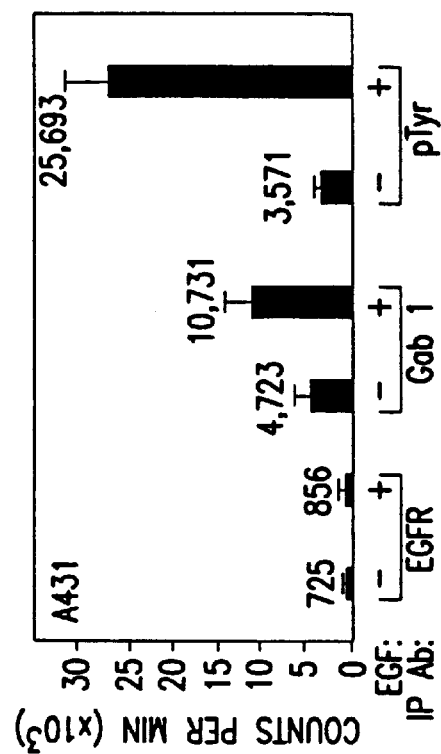
FIG. 4B

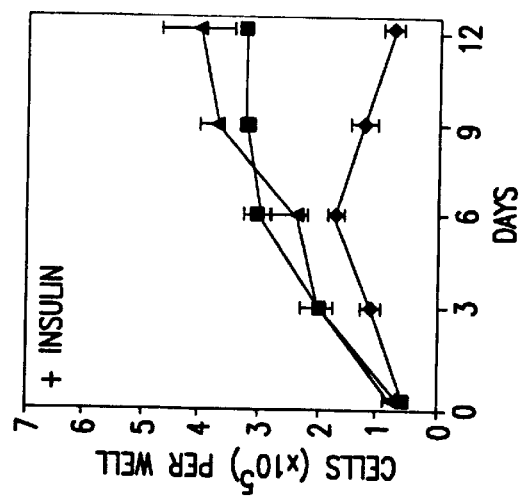
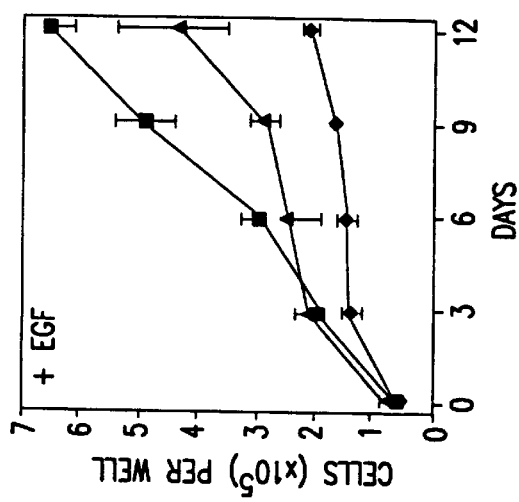
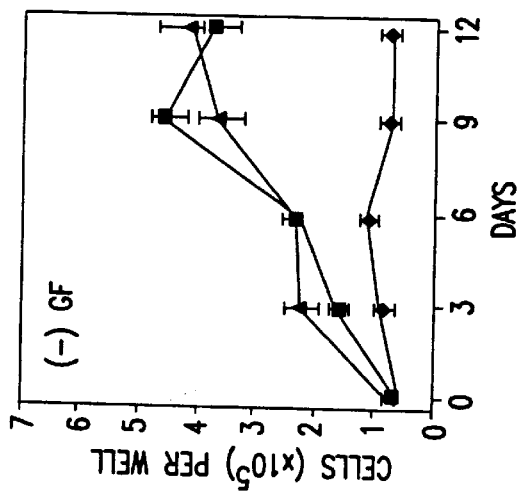
FIG. 4C

GAB1, GRB2 BINDING PROTEIN, AND COMPOSITIONS FOR MAKING AND METHODS OF USING THE SAME

CROSS REFERENCE TO RELATED APPLICATIONS

This application claims the benefit of U.S. Provisional Application No. 60/002,641 filed Aug. 22, 1995.

ACKNOWLEDGMENT OF GOVERNMENT RIGHTS

This invention was made with Government support under Grant NCI P01 NS31102 from the National Cancer Institute. The Government has certain rights in this invention.

FIELD OF THE INVENTION

The invention relates to the identification and cloning of the gene that encodes Grb2 associated binder 1 protein (Gab1), a protein that is involved in tyrosine kinase activation pathways, to isolated Gab1 protein and to methods of making and using the same.

BACKGROUND OF THE INVENTION

Signaling by receptor protein tyrosine kinases (RPTKs) involves the activation of multiple distinct pathways. Grb2 is ubiquitously expressed as a 25 kDa protein that plays a central role in signaling by several receptors (Lowenstein, E. J., et al.(1992) *Cell* 70:431–442 and Downward, J. (1994) *FEBS Letters* 338:113–117). It functions as an adaptor protein where its central SH2 domain binds to an autophosphorylation site on the receptor and the two flanking SH3 domains link to effector molecules. One such target is the mammalian homolog of SOS which is a guanine nucleotide exchange factor for ras, so that Grb2 links receptors with the ras pathway. It is now clear that the SH3 domains also link to a variety of other proteins involved in signaling including Vav (Ren, R., et al. (1994) *Genes Dev.* 8:783–95), c-abl (Ye, Z. S., and Baltimore, D. (1994) *Proc. Natl. Acad. Sci. U.S.A.* 91:12629–12633), dynamin (Gout, I., et al. (1993) *Cell* 75:25–36), and SLP-76 (Jackman, J. K., et al. (1995) *J. Bio. Chem.* 270:7029–7032), but several other binding proteins have been noted during T and B cell signaling (Reif, K. et al. (1994) *J. Biol. Chem.* 269:14081–14087 and Motto, D. G., et al. (1994) *J. Bio. Chem.* 269:21608–21613).

There is a need to identify additional proteins involved in tyrosine kinase activation pathways. There is a need to isolate proteins involved in tyrosine kinase activation pathways, and for compositions and methods for producing and isolating proteins involved in tyrosine kinase activation pathways. There is a need to isolate nucleic acid molecules that encode proteins involved in tyrosine kinase activation pathways. There is a need for compounds which modulate the activity of proteins involved in tyrosine kinase activation pathways. There is a need for kits and methods of identifying such compounds.

SUMMARY OF THE INVENTION

The invention relates to substantially pure proteins that have amino acid sequences shown in SEQ ID NO:2.

The invention relates to pharmaceutical compositions comprising a protein that has the amino acid sequence shown in SEQ ID NO:2 in combination with a pharmaceutically acceptable carrier.

The invention relates to isolated nucleic acid molecules that comprise nucleic acid sequences that encode a protein that has an amino acid sequence shown in SEQ ID NO:2.

The invention relates to pharmaceutical compositions that comprise nucleic acid molecule that comprise nucleic acid sequences that encode a protein that has an amino acid sequence shown in SEQ ID NO:2 in combination with a pharmaceutically acceptable carrier.

The invention relates to isolated nucleic acid molecules that consist of SEQ ID NO:1 or a fragment thereof having at least 5 nucleotides.

The invention relates to a recombinant expression vector comprising the nucleic acid molecule that has a nucleotide sequence that comprises SEQ ID NO:1.

The invention relates to a host cell comprising a recombinant expression vector comprising the nucleic acid molecule that has a nucleotide sequence that comprises SEQ ID NO:1.

The invention relates to an oligonucleotide molecule comprising a nucleotide sequence complimentary to a nucleotide sequence of at least 5 nucleotides of SEQ ID NO:1.

The invention relates to isolated antibodies that bind to an epitope on SEQ ID NO:2.

The invention relates to methods of identifying substrates, activators or inhibitors of Gab1.

The invention relates to methods and kits for identifying compounds that modulate Gab1 phosphorylation by epidermal growth factor receptor (EGFR), insulin receptor, insulin growth factor 1 (IGF-1) receptor, platelet derived growth factor (PDGF) receptor, hepatocyte growth factor (HGF) receptor, TrkA receptor, IL-3 receptor, B cell receptor, or keratinocyte growth factor (KGF) receptor.

The invention relates to methods and kits for identifying compounds that modulate PI-3 kinase protein binding to Gab1 protein.

The invention relates to methods of inhibiting expression of Gab1 by contacting cells that express Gab1 with a nucleic acid molecule that comprises an antisense nucleotide sequence that prevents transcription of Gab1 gene sequences or translation of Gab1 mRNA.

The invention relates to non-human transgenic animals that comprise a transgene which includes a nucleotide sequence that encodes Gab1.

The invention relates to non-human transgenic knock out animals that comprise a nucleotide sequence within the animal's Gab1 gene to render the animal incapable of expressing functional Gab1.

BRIEF DESCRIPTION OF THE FIGURES

FIG. 1 shows the amino acid sequence of Gab1. Potential tyrosine phosphorylation sites which correspond to known motifs for SH2 domains are boxed. These SH2 domains, the respective motif and the positions are: Grb2, Y-X-N-X, ($Y^{48}$); Nck, Y-D-X-P, ($Y^{242}$, $Y^{307}$, $Y^{406}$); PLC-$_{\gamma 1}$, Y-X-I-P, ($Y^{307}$, $Y^{373}$, $Y^{406}$); PI-3-kinase, Y-X-X-M ($Y^{447}$, $Y^{472}$, $Y^{589}$); and SHPTP2/syp2, Y-X-D-L ($Y^{627}$). The predicted site for SHPTP2/syp is derived from the sequence in IRS-1 which has been shown to bind this SH2 domain. The two potential binding sites for the SH3 domains of Grb2 based on the motif P-X-P-X-X-P are shown in bold. The complete nucleotide sequence for Gab1 will be deposited in GenBank.

FIG. 2 shows a sequence comparison illustrating homology between the PH domains of Gab1 and IRS-1. Alignment between amino acid 14–116 of Gab1 with amino acids 13–115 of human IRS-1 (Araki, E. et al. (1993) *Diabetes* 42:1041–1054). Hyphens denote gaps introduced to maximize the alignment, colons indicate amino acid identity and periods denote similarity. For comparison, the consensus sequence deduced for the six conserved subdomains of PH domains (I–VI) is shown below.

FIGS. 4A–4F show results from experiments described in Example 2 which investigate Gab1 mediation of PI-3 kinase activity, cell growth and transformation.

DETAILED DESCRIPTION OF THE INVENTION

Understanding the molecular mechanisms by which the epidermal growth factor (EGF) receptor and insulin receptor transmit their signals within the cell are essential to understanding fundamental processes such as cell growth and differentiation as well as diseases such as cancer and diabetes. The present invention arises out of the discovery of a protein, Gab1 (Grb2 associated binder-1), which is involved in receptor protein signalling pathways. Gab1 is involved in transmitting the signals for, but not limited to, insulin and epidermal growth factor receptors.

Several receptor tyrosine kinases such as the EGF receptor, the neu/HER-2 receptor, the PDGF receptor, and the IGF-1 receptor have been shown to either initiate the cell signalling cascade that leads to tumor formation or to accelerate the growth of tumors. These tyrosine kinases communicate via a complex network of intracellular proteins. In the context of carcinogenic effects, Gab1 is a protein that is directly phosphorylated by at least the EGF and insulin receptor. The phosphorylation of Gab1 then creates binding sites for proteins that are known to result in tumorigenic or tumor promoting effects such as PLC-γ, PI-3-kinase, and SHPTP2/syp. Thus, overexpression of Gab1 in tumors may facilitate the communication by tyrosine kinases to PLC-γ, PI-3-kinase, SHPTP2/syp, etc. and augmenting the tumorigenic or tumor promoting effects.

The action of insulin on cells is communicated via binding to and activation of the insulin receptor, which is also a tyrosine kinase. This receptor phosphorylates several substrates, of which insulin receptor substrate-1 (IRS-1) is the best characterized but not the only substrate. IRS-1 is the prototype of the docking protein family to which Gab1 also belongs. When IRS-1 is phosphorylated by the insulin receptor it communicates the signals for the uptake of glucose and the initiation of cell division. At least some of the molecules that bind to IRS-1 are PI-3-kinase, and SHPTP2/syp, both of which have been shown to be essential to the insulin receptor's effects.

The cDNA that encodes human Gab1 has been cloned and its sequences is shown in SEQ ID NO:1. The amino acid sequence of the protein is shown in SEQ ID NO:2 and FIG. 1. Gab1 was discovered when Far Western blots were performed with the SH3 domains of Grb2 and several bands were detected in glial and medulloblastoma tumors whose size did not correspond to any known protein. cDNA clones for these proteins were obtained using recombinant Grb2 to screen an expression cDNA library from a human glial tumor. The cDNA that encodes Gab1 (Grb2 associated binder-1) was isolated, sequenced and the amino acid sequence of Gab1 protein was predicted. The cDNA that encodes murine Gab1 has also been cloned and its sequences is shown in SEQ ID NO:3. The amino acid sequence of the protein is shown in SEQ ID NO:4.

Figure 1:
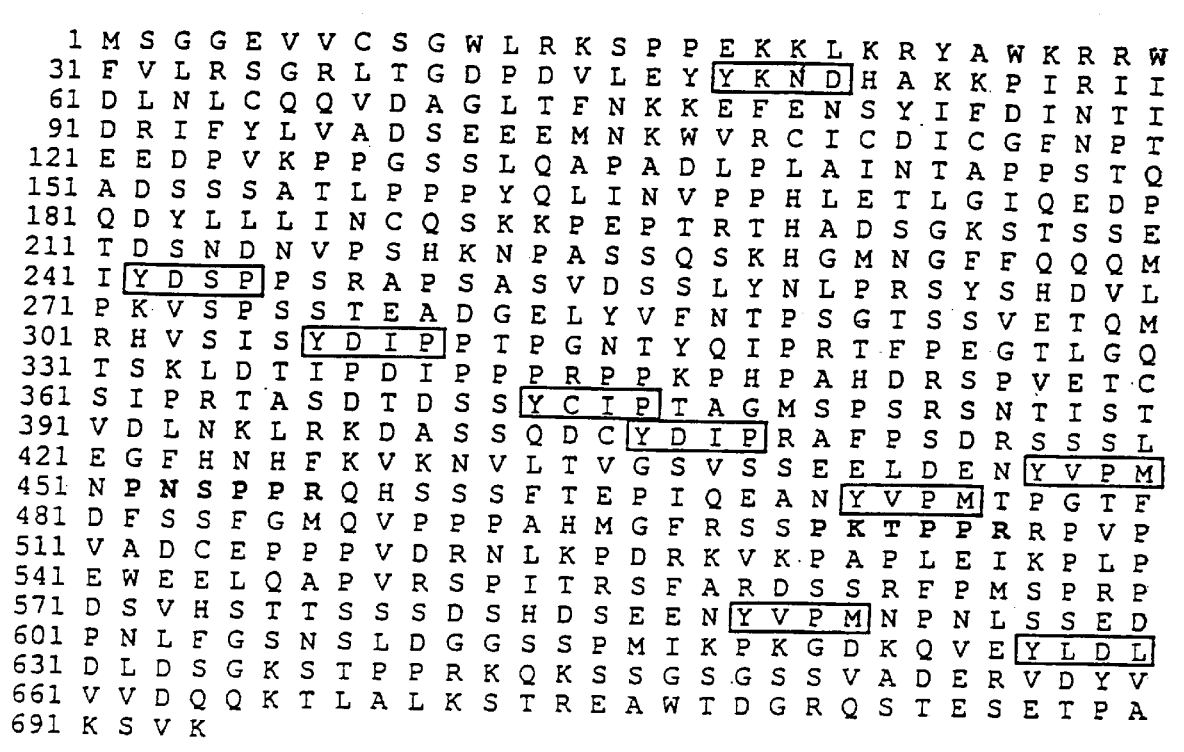
Figure 3:
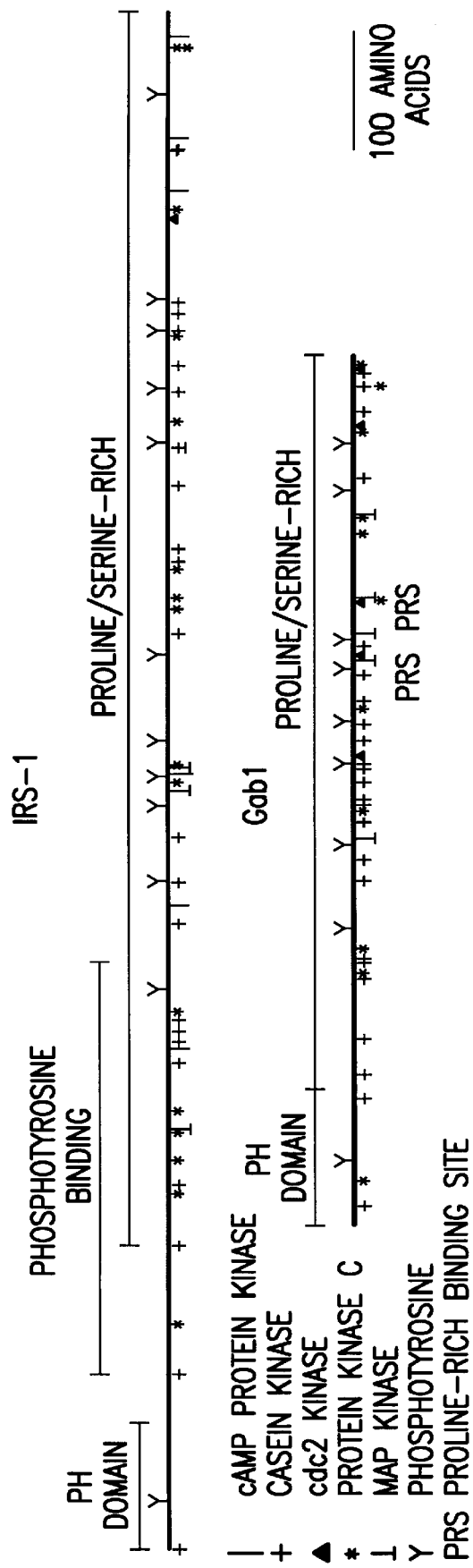
FIG. 3 shows a map depicting the relative distribution for predicted serine/threonine and tyrosine phosphorylation sites in Gab1 compared to those found in human IRS-1. The sites are shown for casein kinase II (S/T-X-X-E/D), cAMP dependent kinase (R/K/R/K-X-S/T), cdc2 kinase (S/T-P-X-K/R), MAP kinase (P-X-S/T-P), and protein kinase C (S/T-X-R/K). Potential tyrosine phosphorylation sites that correspond to predicted binding sites for SH2 domains are shown. Also depicted are structural features including the pleckstrin homology domain (PH domain), the proline/serine rich regions, the bind sites for the SH3 domains of Grb2 (PRS) and the region in IRS-1 that binds to phosphotyrosine (Phosphotyrosine binding).

Analysis of Gab1 indicates that it is highly conserved across species and that it shares amino acid homology and several structural features with IRS-1 (insulin receptor substrate-1) (See FIGS. 2 and 3). As shown in FIGS. 1 and 3, similar to IRS-1, Gab1 has numerous potential phosphorylation sites for tyrosine kinases (Gab 1 has 16 sites for tyrosine phosphorylation) and serine/threonine kinases (Gab1 has 47 sites for serine/threonine phosphorylation). Moreover, Gab1 has an N-terminal pleckstrin homology domain (FIGS. 2 and 3) and binding sites for the growth factor receptor bound-2 (Grb2) protein.

Gab1 is tyrosine phosphorylated by, but not limited to, both the EGF and insulin receptor and like IRS-1; it can act as a docking protein for several SH2-proteins. Generation of an antibody against Gab1 has allowed the observation that, following the addition of EGF or insulin, Gab1 is phosphorylated and this is accompanied by a change in the mobility of the protein on SDS-PAGE. This phosphorylation allows other proteins, including but not limited to PI-3 kinase, SHPTP2/syp, PLC-γ, and Grb2 to bind to Gab1. Gab1 represents a new signaling protein in the EGF and insulin receptor signaling pathways that could integrate the signals from several diverse systems.

The discovery of Gab1 has provided the means to design and discover specific modulators such as inhibitors and activators of this signalling protein. According to the present invention, Gab1 may be used to screen compounds for substrates, inhibitors or activators. Identification of substrates is useful to further elucidate signalling pathways. Inhibitors are useful to interrupt the signalling pathway and are therefore useful to treat neoplasms that are characterized by overexpressed levels of Gab1. Activators are useful as facilitate and enhance Gab1 activity and are therefore useful to treat diabetes characterized by underexpressed or insufficiently functional Gab1. Kits are provided for screening compounds for Gab1 inhibitors. Kits are provided for screening compounds for Gab1 activators. Kits are provided for screening compounds for Gab1 substrates. The nucleotide sequence that encodes the Gab1 is disclosed herein and allows for the production of pure protein, the design of probes which specifically hybridize to nucleic acid molecules that encode Gab1 and antisense compounds to inhibit transcription of Gab1. Anti-Gab1 antibodies are provided. Anti-Gab1 antibodies may be inhibitors of Gab1 and may be used in methods of isolating pure Gab1 and methods of inhibiting Gab1 activity.

One source of Gab1 inhibitor may be compounds designed to resemble portions of Gab1 which interfere with signal transduction processes emanating from Gab1. The basis for such molecules may be either peptides taken directly from the amino acid sequence of Gab1, or variants thereof, or small molecules designed by the aid of computer assisted modeling that would resemble parts of Gab1.

The present invention provides substantially purified human Gab1 which has the amino acid sequence consisting of SEQ ID NO:2. Human Gab1 can be isolated from natural sources, produced by recombinant DNA methods or synthesized by standard protein synthesis techniques. The present invention provides substantially purified murine Gab1 which has the amino acid sequence consisting of SEQ ID NO:4. Murine Gab1 can be isolated from natural sources, produced by recombinant DNA methods or synthesized by standard protein synthesis techniques. Purified Gab1 proteins may be used as a research reagents to study their activity and to identify compounds which modulate their activity. Purified Gab1 proteins may also be used as antigens for generating hybridoma cell lines that produce anti-Gab1 antibodies.

Antibodies which specifically bind to Gab1 may be used to purify the protein from natural sources using well known techniques and readily available starting materials. Such antibodies may also be used to purify Gab1 from material present when producing the protein by recombinant DNA methodology. The present invention relates to antibodies that bind to an epitope which is present on Gab1. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, Gab1 protein, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to Gab1, the hybridoma which produces them is cultured to produce a continuous supply of antibodies.

Using standard techniques and readily available starting materials, nucleic acid molecules that encode a human Gab1 protein may be isolated from a human cDNA library, using probes or primers which are designed using the nucleotide sequence information disclosed in SEQ ID NO:1. Similarly, nucleic acid molecules that encode a murine Gab1 protein may be isolated from a murine cDNA library, using probes or primers which are designed using the nucleotide sequence information disclosed in SEQ ID NO:3.

The present invention relates to an isolated nucleic acid molecule that comprises a nucleotide sequence that encodes human Gab1 that comprises the amino acid sequence of SEQ ID NO:2. In some embodiments, nucleic acid molecules consist of a nucleotide sequence that encodes human Gab1. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing human Gab1 protein.

The present invention also relates to an isolated nucleic acid molecule that comprises a nucleotide sequence that encodes murine Gab1 that comprises the amino acid sequence of SEQ ID NO:4. In some embodiments, nucleic acid molecules consist of a nucleotide sequence that encodes murine Gab1. In some embodiments, the nucleic acid molecules comprise the nucleotide sequence that consists of the coding sequence in SEQ ID NO:3. In some embodiments, the nucleic acid molecules consist of the nucleotide sequence set forth in SEQ ID NO:3. The isolated nucleic acid molecules of the invention are useful to prepare constructs and recombinant expression systems for preparing murine Gab1 protein.

A cDNA library, human or murine, may be generated by well known techniques. A cDNA clone which contains one of the nucleotide sequences set out is identified using probes that comprise at least a portion of the nucleotide sequence disclosed in SEQ ID NO:1 or SEQ ID NO:3. The probes have at least 16 nucleotides, preferably 24 nucleotides. The probes are used to screen the cDNA library using standard hybridization techniques. Alternatively, genomic clones may be isolated using genomic DNA from any human cell as a starting material.

The present invention relates to nucleic acid molecules that hybridize to portions of DNA molecules that encode human Gab1. The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1, PCR primers for amplifying genes and cDNA having SEQ ID NO:1, and antisense molecules for inhibiting transcription and translation of genes and cDNA, respectively, which encode Gab1 having the amino acid sequence of SEQ ID NO:2.

The present invention relates to nucleic acid molecules that hybridize to portion of DNA molecules that encode murine Gab1. The present invention relates to isolated nucleic acid molecules that comprise a nucleotide sequence identical or complementary to a fragment of SEQ ID NO:3 which is at least 10 nucleotides. In some embodiments, the isolated nucleic acid molecules consist of a nucleotide sequence identical or complementary to a fragment of SEQ ID NO:3 which is at least 10 nucleotides. In some embodiments, the isolated nucleic acid molecules comprise or consist of a nucleotide sequence identical or complementary to a fragment of SEQ ID NO:3 which is 15–150 nucleotides. In some embodiments, the isolated nucleic acid molecules comprise or consist of a nucleotide sequence identical or complementary to a fragment of SEQ ID NO:3 which is 15–30 nucleotides. Isolated nucleic acid molecules that comprise or consist of a nucleotide sequence identical or complementary to a fragment of SEQ ID NO:3 which is at least 10 nucleotides are useful as probes for identifying genes and cDNA sequence having SEQ ID NO:3, PCR primers for amplifying genes and cDNA having SEQ ID NO:3, and antisense molecules for inhibiting transcription and translation of genes and cDNA, respectively, which encode Gab1 having the amino acid sequence of SEQ ID NO:4.

The cDNA that encodes human or murine Gab1 may be used as a molecular marker in electrophoresis assays in which cDNA from a sample is separated on an electrophoresis gel and Gab1 probes are used to identify bands which hybridize to such probes. Specifically, SEQ ID NO:1 or portions thereof, may be used as a molecular marker in electrophoresis assays in which cDNA from a sample is separated on an electrophoresis gel and human Gab1 specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes human Gab1. Similarly, SEQ ID NO:3 or portions thereof, may be used as a molecular marker in electrophoresis assays in which cDNA from a sample is separated on an electrophoresis gel and murine Gab1 specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes murine Gab1. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequence in SEQ ID NO:1 may be used to design probes, primers and complimentary molecules which specifically hybridize to the unique nucleotide sequences of human Gab1. The nucleotide sequence in SEQ ID NO:3 may be used to design probes, primers and complimentary molecules which specifically hybridize to the unique nucleotide sequences of murine Gab1. Probes, primers and complimentary molecules which specifically hybridize to nucleotide sequence that encodes human or murine Gab1 may be designed routinely by those having ordinary skill in the art.

The present invention also includes labeled oligonucleotides which are useful as probes for performing oligonucleotide hybridization methods to identify human or murine Gab1 genes and cDNA. Accordingly, the present invention includes probes that can be labelled and hybridized to unique nucleotide sequences of human or murine Gab1. The labelled probes of the present invention are labelled with radiolabeled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequence of human or murine Gab1.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes human or murine Gab1 and insert it into an expression vector using standard techniques and readily available starting materials.

The present invention relates to a recombinant expression vector that comprises a nucleotide sequence that encodes human Gab1 that comprises the amino acid sequence of SEQ ID NO:2. The present invention relates to a recombinant expression vector that comprises a nucleotide sequence that encodes human Gab1 that comprises the amino acid sequence of SEQ ID NO:4. As used herein, the term "recombinant expression vector" is meant to refer to a plasmid, phage, viral particle or other vector which, when introduced into an appropriate host, contains the necessary genetic elements to direct expression of the coding sequence that encodes human or murine Gab1. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence that encodes human Gab1 set forth in SEQ ID NO:1. In some embodiments, the recombinant expression vector comprises the nucleotide sequence that encodes murine Gab1 set forth in SEQ ID NO:3. The recombinant expression vectors of the invention are useful for transforming hosts to prepare recombinant expression systems for preparing human or murine Gab1 protein.

The present invention relates to a host cell that comprises the recombinant expression vector that includes a nucleotide sequence that encodes human Gab1 that comprises SEQ ID NO:2. In some embodiments, the host cell comprises a recombinant expression vector that comprises SEQ ID NO:1. The present invention relates to a host cell that comprises the recombinant expression vector that includes a nucleotide sequence that encodes murine Gab1 that comprises SEQ ID NO:4. In some embodiments, the host cell comprises a recombinant expression vector that comprises SEQ ID NO:3.

Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to transgenic non-human mammals that comprises the recombinant expression vector that comprises a nucleic acid sequence that encodes human Gab1 that comprises the amino acid sequence of SEQ ID NO:2 and to transgenic non-human mammals that comprises the recombinant expression vector that comprises a nucleic acid sequence that encodes murine Gab1 that comprises the amino acid sequence of SEQ ID NO:4. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes human or murine Gab1 is operably linked to a tissue specific promoter whereby the coding sequence is only expressed in that specific tissue. One application is that the tissue specific promoter is a mammary cell specific promoter and the recombinant protein so expressed is recovered from the animal's milk. In some embodiments, the coding sequence that encodes human Gab1 is SEQ ID NO:1. In some embodiments, the coding sequence that encodes murine Gab1 is SEQ ID NO:3.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of Gab1 in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce Gab1 using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes a Gab1 protein is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate Gab1 protein that is produced using such expression systems. The methods of purifying a Gab1 protein from natural sources using antibodies which specifically bind to human or murine Gab1 as described above, may be similarly applied to purifying human or murine Gab1 produced by recombinant DNA methodology.

Examples of genetic constructs include Gab1 coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes a Gab1 protein from readily available starting materials. Such gene constructs are useful for the production of the Gab1 protein.

In some embodiments of the invention, transgenic non-human animals are generated which express human or murine Gab1. The transgenic animals that express human Gab1 according to one embodiment of the invention contain SEQ ID NO:1 under the regulatory control of a mammary specific promoter. The transgenic animals that express human Gab1 according to one embodiment of the invention contain SEQ ID NO:3 under the regulatory control of a tissue specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which express human or murine Gab1 from the transgene. Preferred animals are goats and rodents, particularly rats and mice.

In addition to producing Gab1 by recombinant techniques, automated peptide synthesizers may also be employed to produce human or murine Gab1. Such techniques are well known to those having ordinary skill in the art and are useful if derivatives which have substitutions not provided for in DNA-encoded protein production.

Nucleic acid molecules that encode human Gab1 may be used as part of pharmaceutical compositions for gene therapy. Diseases characterized by underexpression of human Gab1 may include diabetes. Those having ordinary skill in the art can readily identify individuals who are suspected of suffering from such diseases, conditions and disorders using standard diagnostic techniques.

Nucleic acid molecules that encode Gab1 may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In one embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another embodiment of the present invention, nucleic acid is delivered through folate receptor means. The nucleic acid sequence to be delivered to a cell is linked to polylysine and the complex is delivered to cells by means of the folate receptor. U.S. Pat. No. 5,108,921 issued Apr. 28, 1992 to Low et al., which is incorporated herein by reference, describes such delivery components.

Pharmaceutical compositions according to the invention include delivery components in combination with nucleic acid molecules that encode Gab1 which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

According to one aspect of the invention, compounds may be screened to identify human Gab1 inhibitors, activators or substrates. Inhibitors of human Gab1 are useful as antitumor agents. Activators of human Gab1 are useful as diabetes treatment agents. Substrates of human Gab1 are useful as reagents in assays for screening compounds with Gab1 activity and investigating signal pathways.

Inhibitors of human Gab1 may be identified by screening compounds to ascertain their effect on Gab1 activity. In some embodiments of the invention, compounds are screened to identify inhibitors by contacting human Gab1 to Grb2 in the presence or absence of a test compound. Under assay conditions, the inhibitors will prevent or reduce binding of human Gab1 to Grb2. Antibodies which inhibit Gab1/Grb2 binding are useful as inhibitors and, therefore as positive controls in the assay.

Activators of human Gab1 may be identified by screening compounds to ascertain their effect on Gab1/Grb2 binding. In some embodiments of the invention, compounds are screened to identify activators by contacting human Gab1 to Grb2 in the presence or absence of a test compound. Under assay conditions, the activators will enhance, accelerate or increase binding of human Gab1 to Grb2. Antibodies which inhibit Gab1/Grb2 binding are useful as negative controls in the assay.

As used herein, the term substrate is meant to refer to proteins that bind to human Gab1. Cell proteins can be screened to identify those proteins that bind to human Gab1.

Kits are included which comprise containers with reagents necessary to screen test compounds. Such kits include human Gab1 and Grb2, and instructions for performing the assay. Kits may include means to detect and/or measure human Gab1/Grb2 binding such antibodies that bind to human Gab1/Grb2 complex but not uncomplexed proteins or antibodies that bind to uncomplexed proteins but not human Gab1/Grb2 complex. Optionally anti-human Gab1 antibodies are provided as a control.

Drugs that bind to Gab1, which can act as either inhibitors or activators of Gab1 activity, can be obtained through the classic method of screening thousands of small organic compounds. An alternative source for potentially useful compounds would be random peptides derived from chemical synthesis or phage display techniques.

Assays for useful compounds would involve the detection of molecules that bind with a high affinity to Gab1, where either the molecule or Gab1 itself is labeled with an isotope or other such reporter molecule. The assay comprises incubating Gab1 with the test compound and detecting the level of Gab1/test compound binding. Accordingly, the assay comprises Gab1, a test compound and a means to determine the level of binding. Typically, Gab1 is immobilized to a solid phase such as being bound to a solid substrate (such as a bead or plate) and the test compound is labeled and free in solution. Incubation for a period of time (usually 30 min. to overnight) at a set temperature (22°–37° C.) would occur followed by washing with buffer. The solid substrate would then be analyzed for the presence of the reporter molecule. Kits are provided which comprise Gab1, preferably bound to a solid substrate, and a means of distinguishing unbound Gab1 from Gab1 bound to a test compound. Kits may optionally have positive and/or negative controls. Optionally, such kits may also have instructions for performing such assays.

Another embodiment provides an assay to identify molecules that interfere with the binding of other proteins to Gab1. Such proteins include, but are not limited to, the binding of Grb2, PLC-γ, PI-3-kinase, and SHPTP2/syp to Gab1. According to such embodiments, the second protein (e.g., Grb2, PLC-γ, PI-3-kinase, or SHPTP2/syp) and Gab1 are contacted in the presence or absence of a test compound. A means is provided to distinguish Gab1 bound to the second protein from unbound proteins. The level of binding in the presence and absence of the test compound is thereby determined and the capacity of the test compound to inhibit binding is so assessed. One means of distinguishing bound from unbound protein is the use of antibodies that specifically bind to unbound proteins (unbound Gab1 or unbound second protein) but not the Gab1/seconds protein complex or antibodies that specifically bind to the Gab1/seconds protein complex but not unbound proteins (unbound Gab1 or unbound second protein). The use of detectable antibodies is well known. In some embodiments, one of the proteins is immobilized to a solid phase and the second protein is labeled and in solution. The labeled protein is contacted with the fixed protein in the presence or absence of the test compound and the level of labeled protein bound to the fixed protein is measured following a wash of the test compound and unlabeled protein. Some kits are provided which comprise a container with Gab1, a container with Grb2, PLC-γ, PI-3-kinase or SHPTP2/syp, and antibodies which either bind to bound proteins but not unbound or antibodies which bind to either unbound Gab1 or unbound Grb2, PLC-γ, PI-3-kinase or SHPTP2/syp but not bound proteins. Either Gab1 or Grb2, PLC-γ, PI-3-kinase, or SHPTP2/syp are fixed to a solid substrate. Some kits are provided which comprise a container with Gab1 fixed to a solid phase and a container with labeled Grb2, PLC-γ, PI-3-kinase or SHPTP2/syp. Some kits are provided which comprise a container with labeled Gab1 and a container with Grb2, PLC-γ, PI-3-kinase or SHPTP2/syp fixed to a solid phase. Kits may optionally have positive and/or negative controls. Optionally, such kits may also have instructions for performing such assays.

In some embodiments of the invention, methods and kits are provided for identifying compounds that modulate PI-3 kinase protein binding to Gab1 protein. When Gab-1 is phosphorylated, it binds to PI-3 kinase. Gab-1 is a substrate for epidermal growth factor receptor (EGFR), insulin receptor, insulin growth factor 1(IGF-1) receptor, platelet derived growth factor (PDGF) receptor, hepatocyte growth factor (HGF) receptor, TrkA receptor, IL-3 receptor, B cell receptor, or keratinocyte growth factor (KGF) receptor. Thus, by containing the receptor ligand to cells with the receptor such as for example by contacting cells that have EGFRs with EGF or cells with insulin receptors with insulin, Gab1 will be phosphorylated and bind to PI-3 kinase. Gab1 binding to PI-3 kinase is detectable by many different methods including isolation of the Gab1 complexes using anti-Gab1 antibodies. Anti-PI-3 kinase antibodies can be used to detect PI-3 kinase bound to Gab1. Alternatively, PI-3 kinase activity in Gab1 complexes indicates binding of Gab1 to PI-3 kinase. According to the invention, cells that have a particular receptor are contacted with the receptor ligand in the presence (test assay) and absence (control assay) of test compounds. The amount of PI-3 kinase bound to Gab1 in the test assay is compared to the amount of PI-3 bound to Gab1 in the control assay. If PI-3/Gab1 binding is less the test assay, the test compound is indicated to be an inhibitor of PI-3/Gab1 binding. Kits according to the invention can include containers that comprise antibodies that bind to PI-3 and/or containers that comprise antibodies that bind to Gab1 and/or containers comprising reagents for detecting PI-3 kinase activity and/or instructions for performing the assay.

According to another embodiment, an assay is provided to identify compounds that inhibit the phosphorylation of Gab1 by tyrosine kinases such as, for example but not limited to, the EGF and insulin receptors. In some such embodiments, Gab1 is bound to solid substrate, the reaction buffer contains $^{32}P$-γ-ATP and tyrosine kinase is added in the presence or absence of a test compound. Test compounds are identified that result in a decrease in the amount of $^{32}P$ incorporated into Gab1 compared to the level of phosphorylation observed in their absence. Some kits are provided which comprise a container with Gab1 fixed to a solid phase, a container with the reaction buffer contains $^{32}P$-γ-ATP and container with tyrosine kinase. Kits may optionally have positive and/or negative controls. Optionally, such kits may also have instructions for performing such assays.

Another embodiment provides an assay to identify molecules that inhibit the phosphorylation of Gab1 by serine/threonine kinases such as, but not limited to, MAP kinase, cdc2 kinase, protein kinase C, casein kinase, and cAMP kinase. The assay is identical to that above except that a serine/threonine kinase would be used as the source of enzyme. The kits are similar except a container with serine/threonine kinase is provided rather than tyrosine kinase. Kits may optionally have positive and/or negative controls. Optionally, such kits may also have instructions for performing such assays.

In some embodiments of the invention, methods and kits are provided for identifying compounds that modulate Gab1 phosphorylation by epidermal growth factor receptor (EGFR), insulin receptor, insulin growth factor 1(IGF-1) receptor, platelet derived growth factor (PDGF) receptor, hepatocyte growth factor (HGF) receptor, TrkA receptor, IL-3 receptor, B cell receptor, or keratinocyte growth factor (KGF) receptor. Gab-1 is a substrate for epidermal growth factor receptor (EGFR), insulin receptor, insulin growth factor 1(IGF-1) receptor, platelet derived growth factor (PDGF) receptor, hepatocyte growth factor (HGF) receptor, TrkA receptor, IL-3 receptor, B cell receptor, or keratinocyte growth factor (KGF) receptor. Thus, using cells that have a particular receptor and contacting the cells with the receptor ligand, such as for example by contacting cells that have EGFRs with EGF or cells with insulin receptors with insulin, Gab1 will be phosphorylated. Gab1 phosphorylation is detectable by many different methods including electrophoresis. Phosphorylated Gab1 runs as a different size as compared to unphosphorylated Gab1. According to the invention, cells that have a particular receptor are contacted with the receptor ligand in the presence (test assay) and absence (control assay) of test compounds. The amount of phosphorylated Gab1 generated in the test assay is compared to the amount of phosphorylated Gab1 in the control assay. If the test assay has less phosphorylated Gab1, inhibition of Gab1 phosphorylation is indicated, the test compound being an inhibitor. Similarly, if the test assay has more phosphorylated Gab1, enhancement of Gab1 phosphorylation is indicated.

Gab1 has pleckstrin homology (PH) domains. Phosphatidylinositol, 4,5-bisphosphate ($PIP_2$) and the βγ subunits of heterotrimeric G proteins are substrates for the PH domain. Additional embodiments of the invention provide assays to detect molecules that interfere with the binding of $PIP_2$ or βγ subunits to Gab1. Either Gab1 or the substrate is fixed to a solid phase and the other of Gab1 or the substrate is labeled. The binding of Gab1 to the substrate in the presence or absence of a test compound is measured. In some embodiments, the $PIP_2$ or βγ subunits is labeled and free in solution, and the Gab1 is fixed to a solid substrate. The test compound is free in solution. Kits are provided which comprise a container with Gab1 fixed to a solid phase and a container with labeled substrate. Some kits are provided which comprise a container with labeled Gab1 and a container with substrate fixed to a solid phase. Kits may optionally have positive and/or negative controls. Optionally, such kits may also have instructions for performing such assays.

In the various assays of the invention, the preferred concentration of test compound is between 1 μM and 500 μM. A preferred concentration is 10 μM to 100 μM. In some preferred embodiments, it is desirable to use a series of dilutions of test compounds.

It is further contemplated that murine Gab1 may be used in place of human Gab1 in assays and kits for screening compounds to identify human Gab1 inhibitors, activators or substrates.

According to another aspect of the invention, transgenic animals, particularly transgenic mice, are generated. In some embodiments, the transgenic animals according to the invention contain a nucleic acid molecule which encodes human or murine Gab1. Such transgenic mice may be used as animal models for studying overexpression of Gab1 and for use in drug evaluation and discovery efforts to find compounds effective to inhibit or modulate the activity of Gab1, such as for example compounds for treating neoplasms. One having ordinary skill in the art using standard techniques, such as those taught in U.S. Pat. No. 4,873,191 issued Oct. 10, 1989 Wagner and U.S. Pat. No. 4,736,866 issued Apr. 12, 1988 to Leder, both of which are incorporated herein by reference, can produce transgenic animals which produce the human or murine Gab1 and use the animals in drug evaluation and discovery projects.

Another aspect of the present invention relates to knockout mice and methods of using the same. In particular, transgenic mice may be generated which are homozygous for a mutated, non-functional Gab1 gene which is introduced into them using well known techniques. The mice produce no functional Gab1 and are useful to study the function of Gab1. Furthermore, the mice may be used in assays to study the effect of test compounds in Gab1 deficient animals. The Gab1 deficient mice can be used to determine if, how and to what extent Gab1 inhibitors will effect the animal and thereby address concerns associated with inhibiting the activity of the molecule.

Methods of generating genetically deficient "knock out" mice are well known and disclosed in Capecchi, M. R. (1989) *Science* 244:1288–1292 and Li, P. et al. (1995) *CELL* 80:401–411, which are each incorporated herein by reference. The human Gab1 cDNA clone can be used to isolate a murine Gab1 genomic clone. The genomic clone can be used to prepare a Gab1 targeting construct which can disrupt the Gab1 gene in the mouse by homologous recombination.

The targeting construct contains a non-functioning portion of the Gab1 gene which inserts in place of the functioning portion of the native mouse gene. The non-functioning insert generally contains an insertion in the exon that encodes the active region of Gab1. The targeting construct can contain markers for both positive and negative selection. The positive selection marker allows for the selective elimination of cells without it while the negative selection marker allows for the elimination of cells that carry it.

For example, a first selectable marker is a positive marker that will allow for the survival of cells carrying it. In some embodiments, the first selectable marker is an antibiotic resistance gene such as the neomycin resistance gene can be placed within the coding sequences of the Gab1 gene to render it non-functional while additionally rendering the construct selectable. The antibiotic resistance gene is within the homologous region which can recombine with native sequences. Thus, upon homologous reconstruction, the non-functional and antibiotic resistance selectable gene sequences will be taken up. Knock out mice may be used as models for studying diabetes and screening compounds for treating diabetes.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Clones are then injected into the blastocysts and implanted into pseudopregnant females. Chimeric offspring which are capable of transferring the recombinant genes in their germline are selected, mated and their offspring is examined for heterozygous carriers of the recombined genes. Mating of the heterozygous offspring can then be used to generate fully homozygous offspring which are the Gab1 -deficient knock out mouse.

The present invention relates to methods of and compositions for inhibiting the expression of Gab1 in cells. In one embodiment, antisense oligonucleotides are provided which have a nucleotide sequence complementary to a nucleotide sequence of mRNA that encodes human Gab1.

The antisense oligonucleotides of the present invention comprise sequences complementary to regions of human Gab1 mRNA. The oligonucleotides comprise a sequence complementary to a region selected from the sequence of human Gab1 mRNA. The antisense oligonucleotides include single stranded DNA sequence and an antisense RNA oligonucleotide produced from an expression vector. Each of the antisense oligonucleotides of the present invention are complementary to regions of the human Gab1 mRNA sequence.

The antisense oligonucleotides of the present invention comprises a sequence complementary to a fragment of SEQ ID NO:1. See Ullrich et al., *EMBO J.*, 1986, 5:2503, which is incorporated herein by reference. Contemplated by this definition are fragments of oligos within the coding sequence for Gab1. Oligonucleotides are preferably complementary to a nucleotide sequence that is 5–50 nucleotides in length, in some embodiments 8–40, more preferably 12–25 nucleotides, in some embodiments 10–15 nucleotides and in some embodiments 12–20 nucleotides.

In addition, mismatches within the sequences identified above, which achieve the methods of the invention, such that the mismatched sequences are substantially complementary to the Gab1 sequences are also considered within the scope of the disclosure. Mismatches which permit substantial complementarily to the Gab1 sequences will be known to those of skill in the art once armed with the present disclosure. The oligos may also be unmodified or modified by methods well known to those having ordinary skill in the art.

The present invention is also directed to a method of inhibiting Gab1 expression in mammals comprising administering to the mammal an effective amount of an antisense oligonucleotide having a sequence which is complementary to a region of the Gab1 mRNA.

Methods of administering the antisense oligos of the present invention include techniques well known in the art such as and not limited to liposomes, plasmid expression, or viral vector including retroviral vectors. In the administration of oligos via vectors or plasmids, a non-coding RNA strand of Gab1 is preferably used in order to produce antisense RNA oligos which are expressed by the cell. The RNA oligos then bind Gab1 sense or coding RNA sequence.

Methods of administering the oligos to mammals include liposomes, and may be in a mixture with a pharmaceutically acceptable carrier, selected with regard to the intended route of administration and the standard pharmaceutical practice. In addition, antibodies, ligands and the like may be incorporated into the liposomes thereby providing various modes of inhibiting Gab1 expression. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty µg/ml antisense oligo was used for in vitro methods of providing oligos in media for cell growth in culture. This concentration may be extrapolated for in vivo use. The concentration of antisense oligonucleotides for in vivo use is about 40 µg/kg body weight. The in vivo use of the expression vector expressing RNA oligonucleotides is determined by the number of transfected cells.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

Since the phosphorylation status of Gab1 is essential to communicating with other effectors, the degree of phosphorylation may be used in a diagnostic/prognostic assay. One method to assay the degree of tyrosine phosphorylation on Gab1 is to immunoprecipitate Gab1 from tumor lysates and to measure the binding of an anti-phosphotyrosine antibody to Gab1. Antibodies which selectively bind to phosphorylated Gab1 but not unphosphorylated Gab1 or which bind to unphosphorylated Gab1 but not phosphorylated Gab1 may be used to assess the amount of each form of Gab1 in a sample. Since the tyrosine phosphorylation of Gab1 causes a change in mobility of Gab1 on SDS-PAGE, a second method is to perform Western blots on tumor lysates using an anti-Gab1 antibody. This reveals the change in mobility of Gab1 in tumors where presumably tumors would show a shift towards a higher apparent molecular weight (slower mobility on SDS-PAGE). Kits may be provided which include anti-Gab1 antibodies including specific anti-phosphorylated Gab1 antibodies and/or anti-unphosphorylated Gab1 antibodies and instructions for performing the method. Positive and/or negative controls may be optionally provided.

Gab1 is also phosphorylated by the insulin receptor, and since it binds PI-3-kinase and SHPTP2/syp, it is also likely to participate in the physiologic response to insulin. Hence, Gab1 may be involved in diabetes if there is a deficiency of Gab1 in diabetics. This could either be through a failure to express this protein or a mutation in the sequence leading to decreased phosphorylation. This decrease in tyrosine phosphorylation could be assayed in a manner similar to that described above. Kits may be provided which include anti-Gab1 antibodies and instructions for performing the method. Positive and/or negative controls may be optionally provided.

EXAMPLES

Example 1

A cDNA called Gab1 (Grb2 associated binder-1) was identified using recombinant Grb2 to screen an express cDNA library from a human glial tumor. The cDNA library was made as follows. Double selected poly A⁺RNA was isolated from tumor D256. First strand synthesis was performed using random hexamer priming and converted to double stranded cDNA. The products were electrophoresed on acrylamide gels and cDNA above 1 kb was selected for cloning. The vector used for expression was λEXlox (Novagen). Grb2 used to probe the library was expressed in bacteria as a fusion protein with glutathione S-transferase and the phosphorylation site for protein kinase A (Ron, D. and Dressler, H. (1992) *Biotechniques* 13:866–869). Briefly, the cDNA for human Grb2 was cloned in-frame into the pGEX vector (Pharmacia) which was engineered to also carry the site for phosphorylation by protein kinase A. The resulting GST-Grb2 fusion protein was labeled to a specific activity of $1\times10^7$ cpm/µg of protein and $5\times10^5$ cpm/ml was used to screen the library. Purified protein was labeled with $^{32}P$ by an in vitro kinase reaction and then used to screen an expression cDNA library constructed from a glial tumor, 256. Resulting positives were plaque purified twice and then converted to plasmid using the cre-lox system as described by the manufacturer. Six positive clones were identified from ~$2.5\times10^5$ plaques screened, 5 of which were unique as determined by DNA sequencing. One clone, which contained a 1.6 kb insert that did not correspond to any previously described sequence, was used to rescreen oligo dT and hexamer primed libraries from this tumor which resulted in the isolation of 4.2 kb total of the transcript and contained a polyadenylation signal followed by a poly A tract.

Sequencing reactions were performed using di-deoxy terminators coupled to laser fluorochromes (Prism kit, Applied Biosystems) and the reactions run on an ABI 373 A automated sequencer. Primers were used for sequencing on both strands at ~200–400 bp intervals. Sequence analysis revealed the presence of an initiator methionine followed by a 2.1 kb open reading frame. The complete amino acid sequence for Gab1 is presented in SEQ ID NO:2 and shown in FIG. 1. Gab1 encodes a 694 amino acid protein that has a predicted size of 77 kDa. Two putative binding sites for the SH3 domains of Grb2 were identified that were similar to those found in dynamin and SOS (Yu, H., et al (1994) *Cell* 76:933–945). An amino acid homology search revealed that Gab1 was most similar to the human IRS-1, a 130 kDa protein that is one of the major tyrosine phosphorylated proteins following insulin receptor stimulation (Sun, X. J., et al. (1991) *Nature* 352:73–44). The highest degree of homology. (31% identity and 44% similarity) was in the pleckstrin homology (PH) domain that is found in the N-terminus of both proteins (Musacchio, A. et al. (1993) *Trends. Biochem. Sci.* 18:343–344) (FIG. 2). PH domains do not show a high degree of overall homology, but of the known PH domains the Gab1 and IRS-1 PH domains are the most closely related to each other. The similarities between the two proteins extended to other structural features. The distal two-thirds of both proteins are extremely proline and serine rich resulting in numerous potential phosphorylation sites for serine/threonine kinases including cdc2 kinases, protein kinase C, casein kinase and MAP kinase (FIG. 3). There are 5 predicted sites for cdc2 kinase in Gab1 but only one site in IRS-1, while there are not sites for cAMP dependent protein kinase in Gab1 but 6 in IRS-1. Overall, 47 predicted serine/threonine phosphorylation sites can be found in Gab1 and 51 sites such in IRS-1. A key feature of IRS-1 is the presence of 20 potential tyrosine phosphorylation sites. These sites can recruit proteins with SH2 domains enabling IRS-1 to act as a docking protein in signal transduction. It has been shown that Grb2 (Skolnik, E. Y., et al. (1993) *Science* 260:1953–1955), PI-3-kinase, Nck (Lee, C. H., et al. (1993) *Proc. Natl. Acad. U.S.A.* 90:11713–11717), and SHPTP2/syp (Sun, X. J., et al. (1993) *Mol. Cell Biol.* 13:7418–7428) directly interact with IRS-1. Gab1 contains 16 potential binding sites for the SH2 domains of PI-3-kinase, PLC-γ, Nck, and SHPTP2/syp which were identified in Gab1 using the consensus binding motifs for these domains (Songyang, Z., et al.(1994) *Mol. Cell. Biol.* 14:2777–2785 and Songyang, Z., et al. (1993) *Cell* 72:767–778). IRS-1 does contain a phosphotyrosine binding domain (Gustafson, T. A., et al. (1995) *Mol. Cell Bio.* 15:2500–2508) that is not found in Gab1, but the attachment to Grb2 provides an alternate means for Gab1 to associate with receptors. Overall, the similar number of tyrosine and serine/threonine phosphorylation sites in the much smaller Gab1 suggest that it is a compressed version of IRS-1.

Northern blots were prepared using total RNA from tumor 256 or human brain and hybridized with the Gab1 cDNA probe. Briefly, 16 µg of total RNA was electrophoresed in 1% HEPES/formaldehyde gels and transferred to nylon membranes. Standard hybridization and washing conditions were used. The Gab1 cDNA probe detected two transcripts of 4.2 and 7.0 kb in RNA isolated from tumor 256 and human brain. The complete open reading frame of Gab1 could be accounted for in the 4.2 transcript.

Zoo blots were also performed under high stringency conditions to evaluate the species conservation of Gab1. Genomic DNA from human, cow, cat, dog, horse, mouse and pig was restricted with EcoRI and used to prepare Southern blots. Briefly, 10 µg of genomic DNA was digested with EcoRI, electrophoresed in 1% agarose gels and transferred to nylon membranes. Blots were hybridized with the Gab1 cDNA. Normal stringency hybridization and washing conditions were used. Results demonstrated a high degree of conservation across all species tested, including rodents.

Gab1 was observed to interact with Grb2. BL21 bacteria were transformed with an expression plasmid that generated a fusion protein between the gene 10 protein and the proline/serine rich region of Gab1.

GST fusion protein with either Grb2 or Nck was labeled with $^{32}P$ and incubated with Western blots containing lysates from BL21 bacteria that had been transformed with λExlox plasmid encoding for a fragment of Gab1 or no insert. Since the fusion protein generated by λExlox vector is from gene 10, there is no potential of dimerization with the GST portion of the probes.

Far Western blots performed with Grb2 as the probe identified an ~100 kDa protein in cells transformed with the Gab1 fragment but not in cells transformed with plasmid containing no insert. Gab1 is specifically recognized by Grb2.

The apparent size of the fusion protein was ~20 kDa greater than expected and was probably due to the high proline content of this segment. IRS-1 has also been noted to migrate as a larger protein in SDS-PAGE.

In contrast, Nck, which contains three SH3 domains, did not bind the Gab1 fragment indicating that this recognition was not a property of SHS3 domains in general. Preliminary results show that both SH3 domains of Grb2 bind to Gab1 but the C-terminal SH3 domain has a higher affinity.

To confirm that Gab1 can interact with native Grb2, a GST fusion protein was generated with this same fragment from Gab1 (GST-Gab1). This was used in GST precipitation experiments with lysates from A431 cells. A fragment containing amino acids 203–689 of Gab1 was cloned into the pGEX vector and used to produce GST-Gab1 fusion protein for the precipitations. A431 cells were serum starved overnight and then left untreated or stimulated with EGF (100 ng/ml) (human, Gibco/BRL) for 10 min. Cells were lysed in a buffer containing PBS, 1% Triton, 0.5% deoxycholate, 0.1% SDS, 0.004% NaF, 100 µg/ml PMSF, 1 µg/ml aprotinin, 1 µg/ml leupeptin, and 2 mM Na orthovanadate and cleared of insoluble material by centrifugation. 3 µg of GST-Gab1 or GST was incubated with 150 µg of A431 lysate for 30 min. at 4° C., and then incubated with 20 µl of glutathione beads (Pharmacia). The pellet was washed three times with lysis buffer and resuspended in SDS-PAGE sample buffer. One-third of the resulting pellet and supernatant was electrophoresed on SDS-PAGE. The resulting Western blot was incubated with 1 μg/ml of a monoclonal antibody against Grb2 (Upstate Biotechnology, Inc.), washed and then incubated with an $^{125}$I anti-mouse secondary antibody. Western blot analysis of the precipitates using antibodies against Grb2 showed that Grb2 was specifically bound by GST-Gab1 but not by GST protein. This binding did not require the presence of EGF, which was expected since SH3 domain interactions are independent of growth factor addition.

Gab1 was determined to be a substrate for tyrosine kinases. The EGF receptor was observed to phosphorylate Gab1. A431 cells were serum starved overnight and then left untreated or stimulated with EGF for 10 min. Lysates were prepared and EGF receptor was then immunoprecipitated and subsequently used in a kinase reaction with either GST-Gab1 or GST in the presence of $^{32}$P-ATP. A portion of the reaction was then electrophoresed on SDS-PAGE. A band was visible in the GST lane but found to represent minor phosphorylation of the IgG heavy chain. EGF receptor was immunoprecipitated from A431 cells that were treated without or with EGF. This revealed that GST-Gab1, but not GST, was phosphorylated by the EGF receptor which was dependent upon the EGF addition.

Glial tumors frequently express high levels of a naturally occurring deletion within the EGF receptor, called EGFRvIII. This receptor has been shown to be a constitutively active kinase (Ekstrand, A. J., et al. (1994) *Oncogene* 9:2313–2320 and Wong, A. J., et al. (1994) *Sem. Onc.* 21:139–148). The tumor from which Gab1 was isolated predominantly expresses EGFRvIII. When tested to determine whether this receptor could also phosphorylate Gab1, Gab1 was observed to be a substrate for the mutant EGF receptor. In vitro kinase assays were performed using EGFRvIII immunoprecipitated from HC2 20 d2 cells, an NIH-3T3 cell line transfected with the human cDNA for this mutant receptor. The HC2 20 d2 cells were transfected with a cDNA for the EGFRvIII and serum starved overnight. Because the EGFRvIII is constitutively active no stimulation of this receptor was necessary in order to obtain maximal activity. A431 or HC2 20 d2 cells were serum starved for 18 h and stimulated with EGF (100 ng/ml) for 10 min. Cells were lysed and lysates were then subject to immunoprecipitation with an antibody that specifically recognizes this mutant but not the wild type EGF receptor. 10 μg of anti-human EGF receptor antibody (Gibco/BRL) or anti-EGFRvIII was first prebound to 20 μl of protein G/A agarose (Oncogene Science). 1 mg of cell lysate was incubated with the pellet for 2–3 h at 4° C. The pellet was washed 2 times with the same buffer and then washed once with HNTG buffer (150 mM NaCl, 18 mM MgCl$_2$, 10% glycerol, 0.1% Triton and 20 mN Hepes (pH 7.5)). Kinase reactions were then performed in the presence of $^{32}$P-ATP using this receptor and either GST-Gab1 or GST using 1 μg of fusion protein in HNTG buffer with 2.7 μM ATP, 6 mM MnCl$_2$, and 10 μCi of [γ-$^{32}$P] ATP (6000 Ci/mmol) for 15 min. at 4° C. The reaction was stopped by the addition of SDS-PAGE sample buffer. One-third of the reaction was electrophoresed on SDS-PAGE and visualized by autoradiography. GST-Gab1 protein, but not GST, was specifically phosphorylated by this receptor.

Because of the similarity with IRS-1, Gab1 was evaluated as a substrate of the insulin receptor. Insulin receptor phosphorylation of Gab1 was observed. In vitro kinase assays were done using purified insulin receptor. Purified insulin receptor from rat liver was first subjected to an autophosphorylation reaction to avoid interference from the β subunit of the insulin receptor (IR-β). Briefly, 1 mg/ml receptor was incubated in a buffer containing 50 mM Hepes (pH 7.5), 5 mM MnCl$_2$, 2.5 mM ATP, and 100 nM insulin (porcine, Gibco/BRL) at 30° C. for 30 min. This receptor preparation was hen used in kinase assays containing either GST or GST-Gab1 in the presence of $^{32}$P-ATP. Kinase assays were performed using 100 ng of receptor and 1 μg of fusion protein in a final volume of 50 μl using a buffer containing 50 mM Hepes (pH 7.5), 5 mM MnCl$_2$, 50 μM ATP and 0.3 mCi of [γ-$^{32}$P] ATP (6000 Ci/mmol) for 30 min. at 25° C. Using these conditions little β subunit phosphorylation was detected. Results demonstrated that GST-Gab1 was also specifically and highly phosphorylated by this kinase.

To determine if Gab1 is tyrosine phosphorylated in vivo, Gab1 was immunoprecipitated from A431 lysates using an affinity purified Gab1 antibody and the Western blots were incubated with the same antibody. A431 cells were serum starved overnight and then left untreated or stimulated with EGF (100 ng/ml) for 10 min. or insulin (100 nM) for 5 min. Cells were then lysed and used directly for SDS-PAGE or then immunoprecipitated with antiGab1 antibody. 50 μg of cell lysate was run directly on the gel or 1 mg of protein was used for immunoprecipitation with 10 μg/ml of anti-Gab1 antibody. Western blots were incubated with 1 μg/ml of anti-Gab1 antibody or 2 μg/ml of anti-phosphotyrosine antibody (4G10, U.B.I.) followed by $^{125}$I labeled secondary antibody against either rabbit antibody (anti-Gab1) or mouse antibody (4G10) for detection. The anti-Gab1 antibody was raised in rabbits by immunizing with the GST-Gab1 protein. The resulting antisera was affinity purified using GST-Gab1 coupled to agarose (AminoLink, Pierce) and any contaminating antibodies directed against GST were removed by passage over a GST affinity column. Results demonstrated that Gab1 is tyrosine phosphorylated in response to EGF or insulin stimulation. Endogenous Gab1 migrated as an ~115 kDa protein in unstimulated cells. This slower than predicted mobility may be due to a combination of its proline rich nature and serine/threonine phosphorylation in vivo. The addition of EGF resulted in a further decrease in mobility to an apparent size of ~120 kDa. When similar blots were incubated with an anti-phosphotyrosine antibody only the band in EGF stimulated cells was detected. Similar experiments were performed using insulin to stimulate A431 cells. Consistent with the in vitro assays, Gab1 was tyrosine phosphorylated following the addition of insulin. The degree of phosphorylation on Gab1 appeared similar regardless of which growth factor was used.

Having established that Gab1 is tyrosine phosphorylated in vivo, Gab1 was investigated to determine if it could act as a docking protein for SH2-proteins.

Western blots containing anti-Gab1 immunoprecipitations from unstimulated or EGF stimulated A431 cells were incubated with antibodies to Nck, PI-3-kinase, PLC-γ, SHPTP2/syp as well as Grb2. A431 cells were prepared as described above and then 1 mg of protein was used for immunoprecipitations with anti-Gab1 antibody. The blots were divided and the appropriate portion incubated with antibodies against Grb2, Nck, PLC-γ, PI-3-kinase, or SHPTP2/syp. Primary antibodies were used at a concentration of 1 μg/ml. The antibodies used were: anti-Grb2 (U.B.I.); anti-PI-3-kinase (Transduction Laboratories); anti-PLC-γ (U.B.I.); anti-SHPTP2 (Transduction Laboratories); and anti-Nck (Transduction Laboratories). $^{125}$I anti-mouse antibody was used for detection for all these antibodies. PI-3-kinase, PLC-γ, and SHPTP2/syp were all readily detected in immunoprecipitations from EGF treated cells. A band was visible in the immunoprecipitation lanes with the anti-Nck antibody. It was determined to be due to a cross-reaction from the heavy chain of the anti-Gab1 antibody. As expected, Grb2 showed an association with Gab1 in the absence of growth factor, but this association was strongly enhanced by the addition of EGF suggesting further interaction via the SH2 domain. Grb2 has also been noted to associate with Vav or C-ab1 by both SH2 and SH3 domain binding.

To confirm this observation, Far Western blots were performed which verified that the SH2 domain of Grb2 did recognize Gab1 immunoprecipitated from EGF treated cells. Several other proteins with SH2 domains, specifically, the SH2 domains from PLC-γ and PI-3-kinase, but not full length Nck, exhibited strong binding to Gab1 immunoprecipitated from EGF stimulated cells. Portions of the blot containing Gab1 were incubated with GST fusion proteins containing the SH2 domains from Grb2 (Grb2-SH2), both SH2 domains of PLC-γ(PLC-SH2), the N-terminal SH2 domain of PI-3-kinase (PI-3-K(N)SH2) or the C-terminal domain (PI-3-K(C)SH2), or total Nck. Far Western blots were incubated with 5 μg/ml of the GST fusion protein, followed by anti-GST antibody at 1 μg/ml (Santa Cruz Biotechnology), and then $^{125}$I anti-mouse antibody for detection. The portions of the amino acid sequence that these fusion proteins encompassed were: Grb2-SH2, a.a. 50–161 of human Grb2; PI-3-K(N)SH2, a.a. 321–440, and PI-3-K(C)SH2, a.a. 614–724 of human PI-3-kinase; and PLC-SH2, a.a. 540–797 of human PLC-$\gamma_1$. Identical patterns of SH2-protein association were obtained when the A431 cells were stimulated with insulin.

Tyrosine phosphorylation of Gab1 mediates interaction with several proteins that contain SH2 domains. The range of proteins that associate with Gab1 is similar to that of IRS-1 except that IRS-1 binds Nck but fails to bind PLC-γ (White, M. F. (1994) *Curr. Opin. Genet. and Dev.* 4:47–54 and Myers, M. G. and White, M. F. (1993) *Diabetes* 42:643–650).

Multi-site docking proteins could play an important role in integrating signals from proteins that contain SH2 domains. Previously, it had not been clear if docking proteins were necessary for only a few RPTKs or were a more general feature of RPTK mediated signaling. Typically RPTKs possess multiple autophosphorylation sites that can recruit SH2-proteins. The insulin and IGF-1 receptors are unusual in that autophosphorylation does not result in binding of SH2-proteins directly to the receptor so the presence of IRS-1 is critical for signal transmission. However, IRS-1 is specific for these RPTKs since it is not phosphorylated by the EGF or PDGF receptors and IL-4 is the only other growth factor known to cause phosphorylation (Wang, L.-M., et al. (1993) *Proc. Natl. Acad. Sci. U.S.A.* 90:4032–4036). Two related molecules, 4PS and IRS-2 (Tamemoto, H., et al. (1994) *Nature* 372:182–186, Araki, E., et al. (1994) *Nature* 372:186–190 and Tobe, K., et al. (1995) *J. Biol. Chem.* 270:5698–5701), may have a similar specificity. The only other potential docking protein described is p130$^{cas}$ but it primarily has sites for the SH2 domain of c-crk. (Sakai, R., et al. (1994) *EMBO J.* 13:3748–3756). The identification of Gab1 shows that a docking protein is found in the EGF receptor signaling pathway. Other such proteins may be found for other tyrosine kinase receptors.

Unlike IRS-1, Gab1 is the target of the SH3 domains of Grb2. Since the SH2 domain of Grb2 can bind to a wide variety of receptor tyrosine kinases, Gab1 may be positioned downstream of multiple receptors. The SH2 domain of Grb2 can also interact with focal adhesion kinase (FAK) and this mediates signaling by integrins with the ras pathway (Schlaepfer, D. D. et al. (1994) *Nature* 372:786–791). Docking proteins may also have a role in integrin signaling as insulin can promote the associate of IRS-1 with $\alpha^v\beta^3$, although this interaction appears to be specific for this integrin (Vuori, K. and Ruoslahti, E. (1994) *Science* 266:1576–1578). A FAK-Grb2-Gab1 complex may be a more universal means for involving docking proteins in integrin signaling.

PH domain and multiple sites for serine/threonine kinases are present in Gab1. Gab1 may integrate pathways not directly related to tyrosine kinase signaling. The PH domains from β-adrenergic receptor kinase, rasGAP, PLC-γ and BTK have been shown to bind the βγ subunits of G-proteins and this has been localized to the carboxy terminal half of the PH domain for the latter three proteins (Touhara, K. et al. (1994) *J. Biol. Chem.* 269:10217–10220). Gab1 may regulate PH domain proteins linking G-proteins signaling with the ras/MAP kinase pathway. The amino terminal half of several PH domains can bind to phosphatidylinositol-4,5-bisphosphate (Crespo, P. J., et al. (1994) *Nature* 369:418–420). Gab1 may be involved in co-ordinating or otherwise controlling the interaction of PLC-γ with its substrate. Phosphorylation by serine/threonine kinases may provide a means for modulating SH2 or PH domain based interactions with Gab1.

The fact that Gab1 is a substrate of the EGF receptor indicates a role in mediating cell growth and neoplasia. Gab1 is overexpressed in several glial tumors as compared to normal brain. Since it is also phosphorylated by the insulin receptor it may be involved in the cellular response to insulin. Mice in which the IRS-1 gene has been disrupted by homologous recombination show growth retardation but few other abnormalities which may be due to compensatory expression of another docking protein such as Gab1.

Example 2

PI-3-kinase is an enzyme that plays an important role in cell growth and glucose metabolism. While PI-3-kinase is activated following the addition of EGF or insulin to cells, PI-3-kinase does not bind to the EGF or insulin receptor directly. Instead, these receptors phosphorylate other substrates to which PI-3-kinase binds to. It has been shown that in certain cells IRS-1 is the major binding protein for PI-3-kinase following insulin addition.

Experiments were performed to evaluate whether Gab1 serves a similar function in EGF signaling. PI-3 K was assayed using 10 μg anti-EGF receptor. 5 μg anti-Gab1 and 15 μg anti-phosphotyrosine antibody (PY20: Transduction Laboratories) were unsed for immunoprecipitations. Assays were run at least 5 times in duplicate. For transfections, full-length Gab1 cDNA was cloned into pLTR2 and this construct or vector only were co-transfected with pKOneo plasmid into NIH3T3 cells. G418-resistant clones (500 μg/ml$^{-1}$) were subcloned twice by limiting dilution. Cell growth was assayed by seeding 50,000 cells per 35-mm well in DMEM containing 1% calf serum, G418 and the growth factor. For growth in soft agarose, 2,000 cells were suspended in 1 ml of medium containing 0.3% agarose (low-melting Sigma), 10% calf serum, G418 and growth factor, and seeded over a 2-ml 0.6% agarose layer in 35-mm dishes. Cells were fed weekly with 1 ml suspension medium. After three weeks the number of colonies larger than 60 μm was counted. For the MAP kinase mobility shift assay, cell lysates were electrophoresed in 8.5% gels and the subsequent western blots were incubated with an anti-MAP kinase antibody (anti-pan ERK, Transduction Laboratories) which consistently detected ERK2 in these cells. Anti-Sos immunoprecipitations were done using 5 µg of a mouse monoclonal anti-body (Transduction Labs). The results are shown in FIGS. 4A–4F.

Figure 4A:
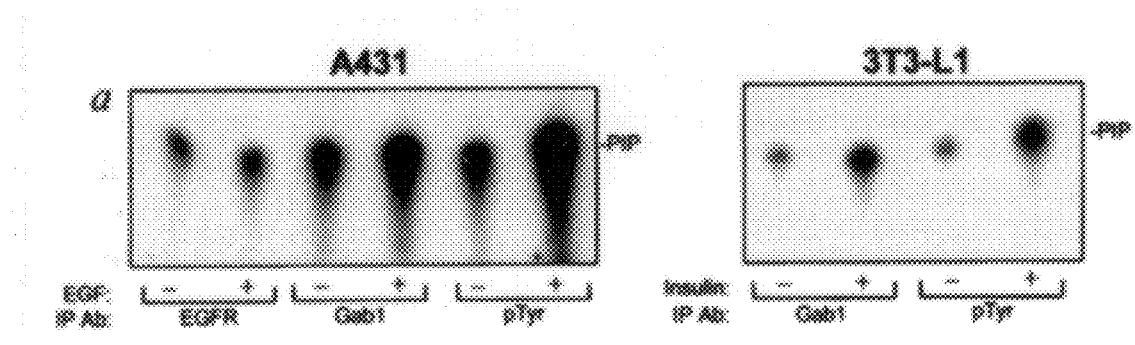

FIG. 4A shows results from experiments in which PI-3 Kinase was assayed on immunoprecipitates (IP) produced by the indicated antibodies (Ab) on lysates from untreated, EGF-stimulated (A431) or insulin-stimulated (3T3-L1) cells, PIP, phosphatidyl-inositol-3-phosphate.

FIG. 4B shows Quantification of the PI(3)K assay. Bars represent average $^{32}P$ c.p.m. values (Cerenkov counts) with s.d. Numbers above the bars designate average c.p.m.

FIG. 4C shows results of Cell-growth assays on the Pilar9 (squares) and the Pilar12 (triangles) cell lines (which express Gab1 at 13- and 8-fold over control (diamonds) cells, respectively) or a vector-only transfected cell line (control) in 1% serum without additional growth factor (-GF) or in the presence of EGF or insulin.

Figure 4D:
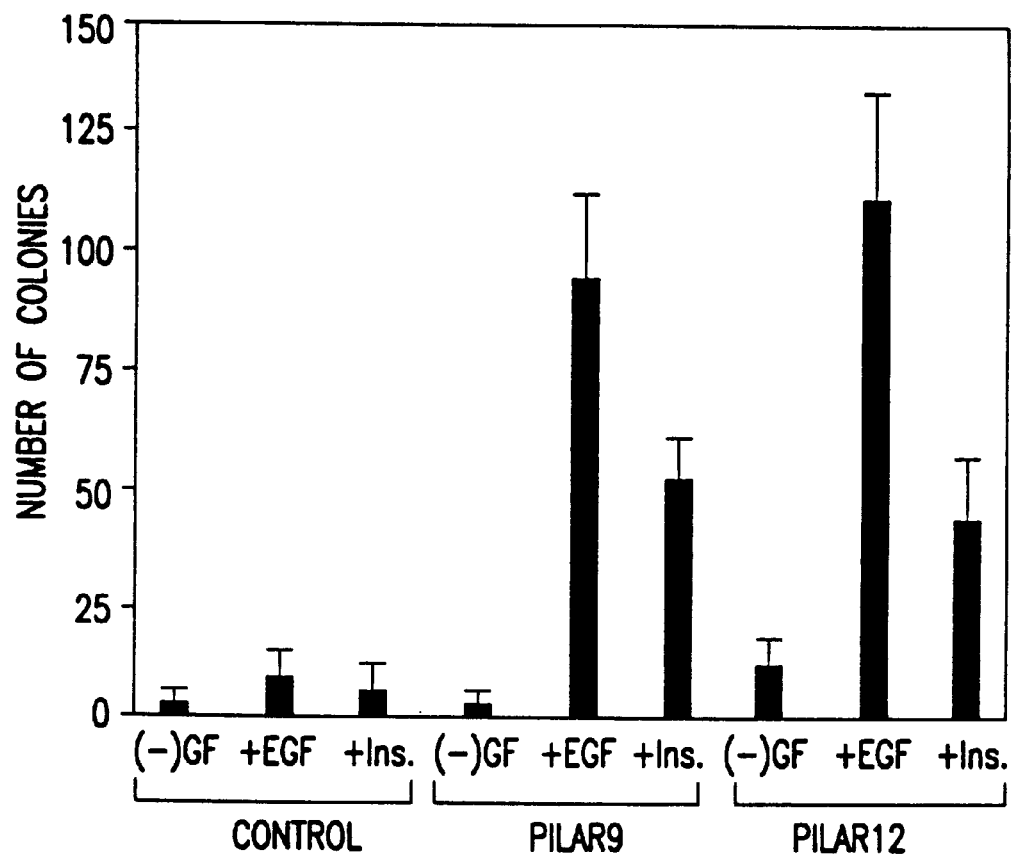

In FIG. 4D, cell lines were seeded in soft agarose and grown in 10% serum without additional growth factor (-GF) or in the presence of EGF or insulin.

Figure 4E:
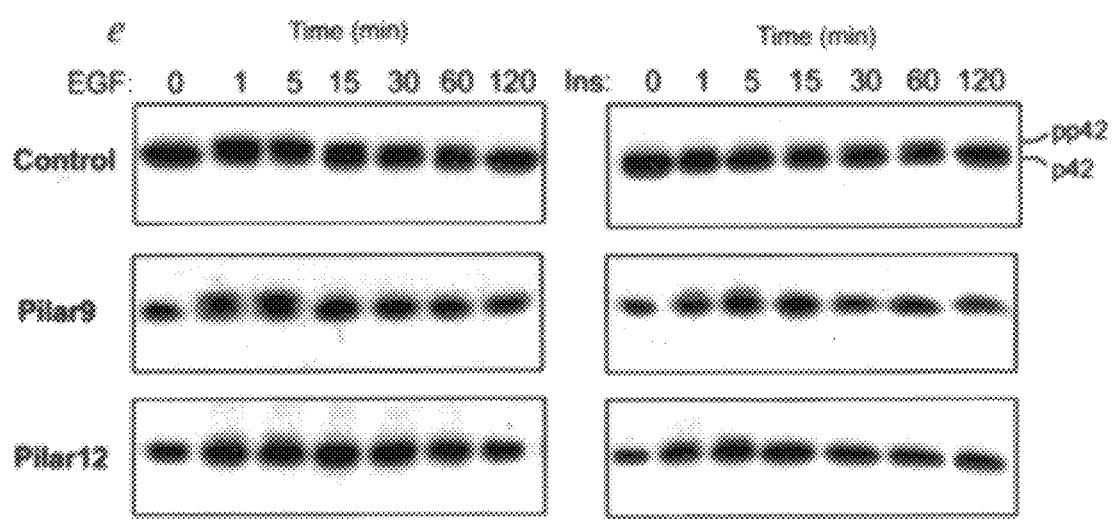

In FIG. 4E, cell lines were serum-starved and then treated with EGF or insulin for the times indicated. Western blots were incubated with an antibody against MAP kinase (p42). Phosphorylated ERK2, which corresponds to the active form, is seen as a slower migrating band (pp-42).

Figure 4F:
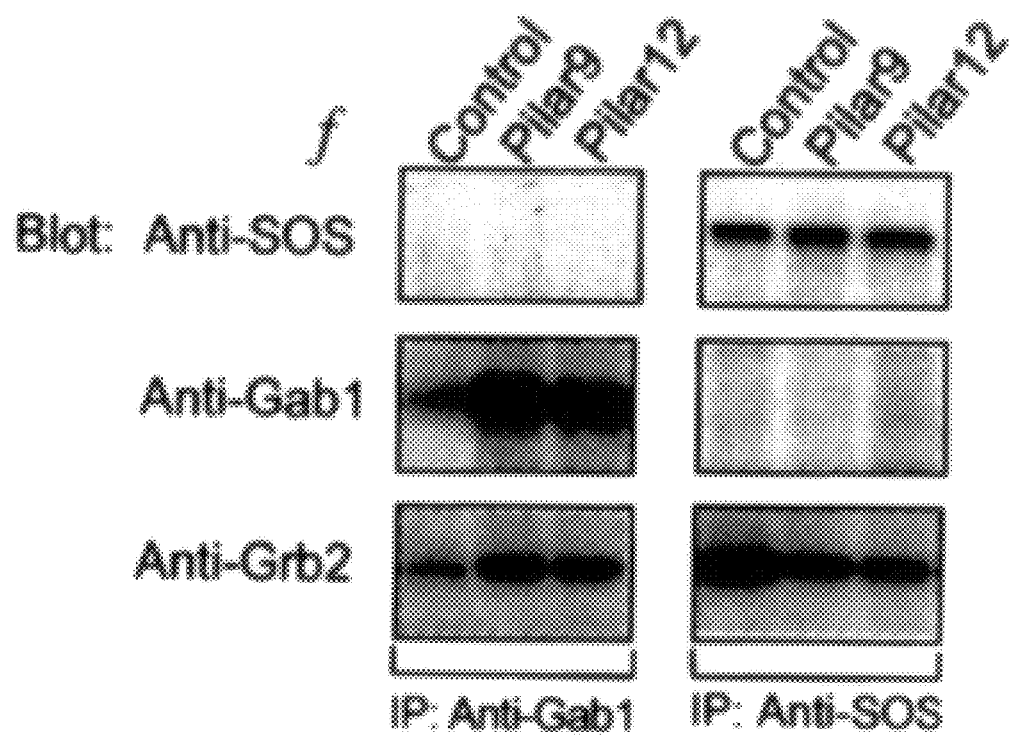

In FIG. 4F, lysates from the cell lines were immunoprecipitated with antibodies against Sos or Gab1. The subsequent western blots were incubated with antibodies against Sos. Gab1 or Grb2.

The results in FIGS. 4A and 4B confirm that EGF stimulation did not produce a substantial increase in PI-3-kinase activity in anti-EGF receptor immunoprecipitates in A431 cells. In addition, these data show that there was PI-3-kinase activity in anti-Gab1 immunoprecipitates in unstimulated cells that increased 2.3 fold upon EGF addition. To measure the overall PI-3-kinase activity of these cells, anti-phosphotyrosine immunoprecipitations were performed. The anti-Gab1 associated activity was 42% of that found in anti-phosphotyrosine immunoprecipitates. In A431 cells, the EGF receptor can transphosphorylate erbB3 and this constitutes ~49% of the anti-phosphotyrosine associated activity indicating that Gab1 and erbB3 are two of the major PI-3-kinase binding proteins after EGF stimulation. Insulin addition produced a 1.7 fold increase in Gab1 immunoprecipitates. 3T3-L1 fibroblasts were also examined for insulin stimulated activity. While the magnitude of the response was lower, insulin produced a 2.4 fold increase in activity. This was 71% of that associated with anti-phosphotyrosine indicating that Gab1 was the major binding partner in these cells following insulin addition. When 3T3-L1 are differentiated into adipocytes PI-3-kinase activity is mainly associated with IRS-1 suggesting a differentiation state specific role for these two docking proteins.

Both EGF and insulin induce mitogenesis and analysis was made to determine if overexpression of Gab1 might augment cell growth. NIH-3T3 cells were transfected with the Gab1 cDNA and two clones, Pilar9 and Pilar12, were selected for further study. The data in FIG. 4C show that both cell lines had an enhanced growth rate and achieved a high cell density in 1% serum whereas control cells failed to proliferate. Growth factor addition did not significantly alter growth, except for Pilar9 where EGF further stimulated growth at high density. These data suggest that Gab1 overexpression rendered NIH-3T3 cells more sensitive to the limiting amount of growth factors present in serum. One measure of transformation is anchorage independent growth. As shown in FIG. 4D, both the Pilar9 and Pilar12 clones exhibited significant colony formation in soft agarose as compared to the control cells. This was dependent on growth factor addition indicating that activation of other proteins was necessary for transformation. Collectively, these data suggest that increased expression of Gab1 could facilitate tumorigenesis by receptor protein tyrosine kinases (RPTKs).

Since SOS and Grb2 can be co-precipitated with IRS-1, it has been suggested that IRS-1 participates in the activation of MAP kinase via the ras pathway. The Gab1 transfected clones were examined to determine if they showed any enhancement of MAP kinase activation. As shown in FIG. 4E, control cells showed a large and sustained increase in MAP kinase phosphorylation following addition of growth factor, but the Pilar9 and Pilar12 clones showed only a small and attenuated duration of activation. We then examined if SOS could co-precipitate with Gab1. As shown iun FIG. 4F, while Grb2 was found in anti-SOS or anti-Gab1 immunoprecipitates, SOS could not be detected in anti-Gab1 complexes nor could Gab1 be found in anti-SOS complexes. The amount of Grb2 that co-precipitated with SOS was decreased in the Pilar9 and Pilar12 clones, so an explanation for the decrease in MAP kinase activity is that Gab1 competes with SOS for binding to Grb2. While it is not clear if Gab1 regulates SOS and the ras pathway under normal conditions, these results show that overexpression of Gab1 does not enhance MAP kinase activation and that Gab1 and SOS form separate complexes with Grb2. These findings are consistent with recent data showing that IRS-1 is not directly involved in MAP kinase activation by insulin.

Example 3

Gab1 has been observed to be a substrate for the insulin-like growth factor 1(IGF-1) receptor, platelet derived growth factor (PDGF) receptor, hepatocyte growth factor (HGF) receptor, TrkA receptor, IL-3 receptor, B cell receptor, and keratinocyte growth factor (KGF) receptor. This implicates Gab1 in potentially a wide variety of physiologic situations. Two receptors where Gab1 may play a particularly central role are the HGF and TrkA receptors. Specifically, following activation of the HGF receptor, it has been observed that Gab1 is the major tyrosine phosphorylated substrate of this receptor. This is an important finding as the HGF receptor has been shown to play an essential role in the genesis of hepatocellular carcinoma. In development, deletion of the HGF receptor in a mouse knock-out model results in loss of igration of certain muscle cells such as the ones that constitute the diaphragm and the long muscles of the body. The TrkA receptor is the receptor for the 2.5S form of nerve growth factor (NGF). Both NGF and the TrkA receptor are required for the proper development of the sympathetic nervous system as in mice which have undergone a homozygous deletion for either gene lack sympathetic neurons. A 115 kd protein has been described as one of the major tyrosine phosphorylated substrates of the TrkA receptor. This 115 kd protein is Gab1. The activation of the enzyme PI-3-kinase by the TrkA receptor is also essential for normal neuronal cell function. Gab1 acts as the major site of recruitment of PI-3-kinase activity in these cells following activation of TrkA receptor by NGF addition.

We claim:

1. A substantially pure protein comprising the amino acid sequence of SEQ ID NO:2.
2. The protein of claim 1 wherein said protein has the amino acid sequence of SEQ ID NO:2.
3. An isolated nucleic acid molecule that encodes a protein having the amino acid sequence of SEQ ID NO:2.
4. The nucleic acid molecule of claim 3 comprising SEQ ID NO:1.
5. A recombinant expression vector comprising the nucleic acid molecule of claim 4.
6. A host cell comprising the recombinant expression vector of claim 5.
7. An isolated nucleic acid molecule that comprises a nucleic acid sequence that encodes SEQ ID NO:2.
8. The nucleic acid molecule of claim 7 having SEQ ID NO:1.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2467 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 122..2203

(xi) SEQUENCE DESCRIPTION: SEQ ID NO:1:

```
ACCTCTGGTG GTGGCTGGCT ACTCGGATAC GAATTCGGCA CGAGGGCAGG CGTCGGCTAG        60

TGTCGGGAGT CGCGCCCGCC GCCCCTCAGC TGCCCGGCCC GGAGCCCGAG ACGCGCGCAC       120

CCC ATG AGC GGT GGT GAA GTG GTC TGC TCC GGA TGG CTC CGC AAG TCC        166
    Met Ser Gly Gly Glu Val Val Cys Ser Gly Trp Leu Arg Lys Ser
    1               5                   10                  15

CCC CCG GAG AAA AAG TTG AAG CGT TAT GCA TGG AAG AGG AGA TGG TTC        214
Pro Pro Glu Lys Lys Leu Lys Arg Tyr Ala Trp Lys Arg Arg Trp Phe
                20                  25                  30

GTG TTA CGC AGT GGC CGT TTA ACT GGA GAT CCA GAT GTT TTG GAA TAT        262
Val Leu Arg Ser Gly Arg Leu Thr Gly Asp Pro Asp Val Leu Glu Tyr
            35                  40                  45

TAC AAA AAT GAT CAT GCC AAG AAG CCT ATT CGT ATT ATT GAT TTA AAT        310
Tyr Lys Asn Asp His Ala Lys Lys Pro Ile Arg Ile Ile Asp Leu Asn
        50                  55                  60

TTA TGT CAA CAA GTA GAT GCT GGA TTG ACA TTT AAC AAA AAA GAG TTT        358
Leu Cys Gln Gln Val Asp Ala Gly Leu Thr Phe Asn Lys Lys Glu Phe
    65                  70                  75

GAA AAC AGC TAC ATT TTT GAT ATC AAC ACT ATT GAC CGG ATT TTC TAC        406
Glu Asn Ser Tyr Ile Phe Asp Ile Asn Thr Ile Asp Arg Ile Phe Tyr
80                  85                  90                  95

TTG GTA GCA GAC AGC GAG GAG GAG ATG AAT AAG TGG GTT CGT TGT ATT        454
Leu Val Ala Asp Ser Glu Glu Glu Met Asn Lys Trp Val Arg Cys Ile
                100                 105                 110

TGT GAC ATC TGT GGG TTT AAT CCA ACA GAA GAA GAT CCT GTG AAG CCA        502
Cys Asp Ile Cys Gly Phe Asn Pro Thr Glu Glu Asp Pro Val Lys Pro
            115                 120                 125

CCT GGC AGC TCT TTA CAA GCA CCA GCT GAT TTA CCT TTA GCT ATA AAT        550
Pro Gly Ser Ser Leu Gln Ala Pro Ala Asp Leu Pro Leu Ala Ile Asn
        130                 135                 140

ACA GCA CCA CCA TCC ACC CAG GCA GAT TCA TCC TCT GCT ACT CTA CCT        598
Thr Ala Pro Pro Ser Thr Gln Ala Asp Ser Ser Ser Ala Thr Leu Pro
    145                 150                 155

CCT CCA TAT CAG CTA ATC AAT GTT CCA CCA CAC CTG GAA ACT CTT GGC        646
Pro Pro Tyr Gln Leu Ile Asn Val Pro Pro His Leu Glu Thr Leu Gly
160                 165                 170                 175

ATT CAG GAG GAT CCT CAA GAC TAC CTG TTG CTC ATC AAC TGT CAA AGC        694
Ile Gln Glu Asp Pro Gln Asp Tyr Leu Leu Leu Ile Asn Cys Gln Ser
                180                 185                 190

AAG AAG CCC GAA CCC ACC AGA ACG CAT GCT GAT TCT GGA AAA TCC ACC        742
Lys Lys Pro Glu Pro Thr Arg Thr His Ala Asp Ser Gly Lys Ser Thr
            195                 200                 205
```

| | | | | | | | | | | | | | | | | |
|---|---|---|---|---|---|---|---|---|---|---|---|---|---|---|---|---|
| TCT | TCT | GAA | ACA | GAC | TCC | AAT | GAT | AAC | GTC | CCT | TCT | CAT | AAA | AAT | CCT | 790 |
| Ser | Ser | Glu | Thr | Asp | Ser | Asn | Asp | Asn | Val | Pro | Ser | His | Lys | Asn | Pro | |
| | | 210 | | | | | 215 | | | | | 220 | | | | |
| GCT | TCC | TCC | CAG | AGC | AAA | CAT | GGA | ATG | AAT | GGC | TTT | TTT | CAG | CAG | CAA | 838 |
| Ala | Ser | Ser | Gln | Ser | Lys | His | Gly | Met | Asn | Gly | Phe | Phe | Gln | Gln | Gln | |
| | 225 | | | | | 230 | | | | | 235 | | | | | |
| ATG | ATA | TAC | GAC | TCT | CCA | CCT | TCA | CGT | GCC | CCA | TCT | GCT | TCA | GTT | GAC | 886 |
| Met | Ile | Tyr | Asp | Ser | Pro | Pro | Ser | Arg | Ala | Pro | Ser | Ala | Ser | Val | Asp | |
| 240 | | | | | 245 | | | | | 250 | | | | | 255 | |
| TCC | AGC | CTT | TAT | AAC | CTG | CCC | AGG | AGT | TAT | TCC | CAT | GAT | GTT | TTA | CCA | 934 |
| Ser | Ser | Leu | Tyr | Asn | Leu | Pro | Arg | Ser | Tyr | Ser | His | Asp | Val | Leu | Pro | |
| | | | | 260 | | | | | 265 | | | | | 270 | | |
| AAG | GTG | TCT | CCA | TCA | AGT | ACT | GAA | GCA | GAT | GGA | GAA | CTC | TAT | GTT | TTT | 982 |
| Lys | Val | Ser | Pro | Ser | Ser | Thr | Glu | Ala | Asp | Gly | Glu | Leu | Tyr | Val | Phe | |
| | | | 275 | | | | | 280 | | | | | 285 | | | |
| AAT | ACC | CCA | TCT | GGG | ACA | TCG | AGT | GTA | GAG | ACT | CAA | ATG | AGG | CAT | GTA | 1030 |
| Asn | Thr | Pro | Ser | Gly | Thr | Ser | Ser | Val | Glu | Thr | Gln | Met | Arg | His | Val | |
| | | 290 | | | | | 295 | | | | | 300 | | | | |
| TCT | ATT | AGT | TAT | GAC | ATT | CCT | CCA | ACA | CCT | GGT | AAT | ACT | TAT | CAG | ATT | 1078 |
| Ser | Ile | Ser | Tyr | Asp | Ile | Pro | Pro | Thr | Pro | Gly | Asn | Thr | Tyr | Gln | Ile | |
| | 305 | | | | | 310 | | | | | 315 | | | | | |
| CCA | CGA | ACA | TTT | CCA | GAA | GGA | ACC | TTG | GGA | CAG | ACA | TCA | AAG | CTA | GAC | 1126 |
| Pro | Arg | Thr | Phe | Pro | Glu | Gly | Thr | Leu | Gly | Gln | Thr | Ser | Lys | Leu | Asp | |
| 320 | | | | | 325 | | | | | 330 | | | | | 335 | |
| ACT | ATT | CCA | GAT | ATT | CCT | CCA | CCT | CGG | CCA | CCG | AAA | CCA | CAT | CCA | GCT | 1174 |
| Thr | Ile | Pro | Asp | Ile | Pro | Pro | Pro | Arg | Pro | Pro | Lys | Pro | His | Pro | Ala | |
| | | | 340 | | | | | 345 | | | | | 350 | | | |
| CAT | GAC | CGA | TCT | CCT | GTG | GAA | ACG | TGT | AGT | ATC | CCA | CGC | ACC | GCC | TCA | 1222 |
| His | Asp | Arg | Ser | Pro | Val | Glu | Thr | Cys | Ser | Ile | Pro | Arg | Thr | Ala | Ser | |
| | | | 355 | | | | | 360 | | | | | 365 | | | |
| GAC | ACT | GAC | AGT | AGT | TAC | TGT | ATC | CCT | ACA | GCA | GGG | ATG | TCG | CCT | TCA | 1270 |
| Asp | Thr | Asp | Ser | Ser | Tyr | Cys | Ile | Pro | Thr | Ala | Gly | Met | Ser | Pro | Ser | |
| | | 370 | | | | | 375 | | | | | 380 | | | | |
| CGT | AGT | AAT | ACC | ATT | TCC | ACT | GTG | GAT | TTA | AAC | AAA | TTG | CGA | AAA | GAT | 1318 |
| Arg | Ser | Asn | Thr | Ile | Ser | Thr | Val | Asp | Leu | Asn | Lys | Leu | Arg | Lys | Asp | |
| | 385 | | | | | 390 | | | | | 395 | | | | | |
| GCT | AGT | TCT | CAA | GAC | TGC | TAT | GAT | ATT | CCA | CGA | GCA | TTT | CCA | AGT | GAT | 1366 |
| Ala | Ser | Ser | Gln | Asp | Cys | Tyr | Asp | Ile | Pro | Arg | Ala | Phe | Pro | Ser | Asp | |
| 400 | | | | | 405 | | | | | 410 | | | | | 415 | |
| AGA | TCT | AGT | TCA | CTT | GAA | GGC | TTC | CAT | AAC | CAC | TTT | AAA | GTC | AAA | AAT | 1414 |
| Arg | Ser | Ser | Ser | Leu | Glu | Gly | Phe | His | Asn | His | Phe | Lys | Val | Lys | Asn | |
| | | | | 420 | | | | | 425 | | | | | 430 | | |
| GTG | TTG | ACA | GTG | GGA | AGT | GTT | TCA | AGT | GAA | GAA | CTG | GAT | GAA | AAT | TAC | 1462 |
| Val | Leu | Thr | Val | Gly | Ser | Val | Ser | Ser | Glu | Glu | Leu | Asp | Glu | Asn | Tyr | |
| | | | 435 | | | | | 440 | | | | | 445 | | | |
| GTC | CCA | ATG | AAT | CCC | AAT | TCA | CCA | CCA | CGA | CAA | CAT | TCC | AGC | AGT | TTT | 1510 |
| Val | Pro | Met | Asn | Pro | Asn | Ser | Pro | Pro | Arg | Gln | His | Ser | Ser | Ser | Phe | |
| | | 450 | | | | | 455 | | | | | 460 | | | | |
| ACA | GAA | CCA | ATT | CAG | GAA | GCA | AAT | TAT | GTG | CCA | ATG | ACT | CCA | GGA | ACA | 1558 |
| Thr | Glu | Pro | Ile | Gln | Glu | Ala | Asn | Tyr | Val | Pro | Met | Thr | Pro | Gly | Thr | |
| | 465 | | | | | 470 | | | | | 475 | | | | | |
| TTT | GAT | TTT | TCC | TCA | TTT | GGA | ATG | CAA | GTT | CCT | CCT | CCT | GCT | CAT | ATG | 1606 |
| Phe | Asp | Phe | Ser | Ser | Phe | Gly | Met | Gln | Val | Pro | Pro | Pro | Ala | His | Met | |
| 480 | | | | | 485 | | | | | 490 | | | | | 495 | |
| GGC | TTC | AGG | TCC | AGC | CCA | AAA | ACC | CCT | CCC | AGA | AGG | CCA | GTT | CCT | GTT | 1654 |
| Gly | Phe | Arg | Ser | Ser | Pro | Lys | Thr | Pro | Pro | Arg | Arg | Pro | Val | Pro | Val | |
| | | | | 500 | | | | | 505 | | | | | 510 | | |
| GCA | GAC | TGT | GAA | CCA | CCC | CCC | GTG | GAT | AGG | AAC | CTC | AAG | CCA | GAC | AGA | 1702 |
| Ala | Asp | Cys | Glu | Pro | Pro | Pro | Val | Asp | Arg | Asn | Leu | Lys | Pro | Asp | Arg | |
| | | | 515 | | | | | 520 | | | | | 525 | | | |

```
AAA GTC AAG CCA GCG CCT TTA GAA ATA AAA CCT TTG CCA GAA TGG GAA        1750
Lys Val Lys Pro Ala Pro Leu Glu Ile Lys Pro Leu Pro Glu Trp Glu
        530                 535                 540

GAA TTA CAA GCC CCA GTT AGA TCT CCC ATC ACT AGG AGT TTT GCT CGA        1798
Glu Leu Gln Ala Pro Val Arg Ser Pro Ile Thr Arg Ser Phe Ala Arg
545                 550                 555

GAC TCT TCC AGG TTT CCC ATG TCC CCC CGA CCA GAT TCA GTG CAT AGC        1846
Asp Ser Ser Arg Phe Pro Met Ser Pro Arg Pro Asp Ser Val His Ser
560                 565                 570                 575

ACA ACT TCA AGC AGT GAC TCA CAC GAC AGT GAA GAG AAT TAT GTT CCC        1894
Thr Thr Ser Ser Ser Asp Ser His Asp Ser Glu Glu Asn Tyr Val Pro
                580                 585                 590

ATG AAC CCA AAC CTG TCC AGT GAA GAC CCA AAT CTC TTT GGC AGT AAC        1942
Met Asn Pro Asn Leu Ser Ser Glu Asp Pro Asn Leu Phe Gly Ser Asn
            595                 600                 605

AGT CTT GAT GGA GGA AGC AGC CCT ATG ATC AAG CCC AAA GGA GAC AAA        1990
Ser Leu Asp Gly Gly Ser Ser Pro Met Ile Lys Pro Lys Gly Asp Lys
        610                 615                 620

CAG GTG GAA TAC TTA GAT CTC GAC TTA GAT TCT GGG AAA TCC ACA CCA        2038
Gln Val Glu Tyr Leu Asp Leu Asp Leu Asp Ser Gly Lys Ser Thr Pro
625                 630                 635

CCA CGT AAG CAA AAG AGC AGT GGC TCA GGC AGC AGT GTA GCA GAT GAG        2086
Pro Arg Lys Gln Lys Ser Ser Gly Ser Gly Ser Ser Val Ala Asp Glu
640                 645                 650                 655

AGA GTG GAT TAT GTT GTT GTT GAC CAA CAG AAG ACC TTG GCT CTA AAG        2134
Arg Val Asp Tyr Val Val Val Asp Gln Gln Lys Thr Leu Ala Leu Lys
                660                 665                 670

AGT ACC CGG GAA GCC TGG ACA GAT GGG AGA CAG TCC ACA GAA TCA GAA        2182
Ser Thr Arg Glu Ala Trp Thr Asp Gly Arg Gln Ser Thr Glu Ser Glu
            675                 680                 685

ACG CCA GCG AAG AGT GTG AAA TGAAAATATT GCCTTGCCAT TTCTGAACAA          2233
Thr Pro Ala Lys Ser Val Lys
        690

AAGAAAACTG AATTGTAAAG ATAAATCCCT TTTGAAGAAT GACTTGACAC TTCCACTCTA     2293

GGTAGATCCT CAAATGAGTA GAGTTGAAGT CAAAGGACCT TTCTGACATA ATCAAGCAAT     2353

TTAGACTTAA GTGGTGCTTT GTGGTATCTG AACAATTCAT AACATGTAAA TAATGTGGGA     2413

AAATAGTATT GTTTAGCTCC CAGAGAAACA TTTGTTCCAC AGTTAACACA CTCG           2467

(2) INFORMATION FOR SEQ ID NO:2:

(i) SEQUENCE CHARACTERISTICS:
        (A) LENGTH: 694 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gly Gly Glu Val Val Cys Ser Gly Trp Leu Arg Lys Ser Pro
1               5                   10                  15

Pro Glu Lys Lys Leu Lys Arg Tyr Ala Trp Lys Arg Arg Trp Phe Val
            20                  25                  30

Leu Arg Ser Gly Arg Leu Thr Gly Asp Pro Asp Val Leu Glu Tyr Tyr
        35                  40                  45

Lys Asn Asp His Ala Lys Lys Pro Ile Arg Ile Ile Asp Leu Asn Leu
    50                  55                  60

Cys Gln Gln Val Asp Ala Gly Leu Thr Phe Asn Lys Lys Glu Phe Glu
65                  70                  75                  80

Asn Ser Tyr Ile Phe Asp Ile Asn Thr Ile Asp Arg Ile Phe Tyr Leu
```

```
                        85                  90                  95
Val Ala Asp Ser Glu Glu Met Asn Lys Trp Val Arg Cys Ile Cys
                100                 105                 110
Asp Ile Cys Gly Phe Asn Pro Thr Glu Glu Asp Pro Val Lys Pro Pro
                115                 120                 125
Gly Ser Ser Leu Gln Ala Pro Ala Asp Leu Pro Leu Ala Ile Asn Thr
            130                 135                 140
Ala Pro Pro Ser Thr Gln Ala Asp Ser Ser Ala Thr Leu Pro Pro
145                 150                 155                 160
Pro Tyr Gln Leu Ile Asn Val Pro Pro His Leu Glu Thr Leu Gly Ile
                165                 170                 175
Gln Glu Asp Pro Gln Asp Tyr Leu Leu Leu Ile Asn Cys Gln Ser Lys
                180                 185                 190
Lys Pro Glu Pro Thr Arg Thr His Ala Asp Ser Gly Lys Ser Thr Ser
                195                 200                 205
Ser Glu Thr Asp Ser Asn Asp Asn Val Pro Ser His Lys Asn Pro Ala
                210                 215                 220
Ser Ser Gln Ser Lys His Gly Met Asn Gly Phe Phe Gln Gln Met
225                 230                 235                 240
Ile Tyr Asp Ser Pro Pro Ser Arg Ala Pro Ser Ala Ser Val Asp Ser
                245                 250                 255
Ser Leu Tyr Asn Leu Pro Arg Ser Tyr Ser His Asp Val Leu Pro Lys
                260                 265                 270
Val Ser Pro Ser Ser Thr Glu Ala Asp Gly Glu Leu Tyr Val Phe Asn
                275                 280                 285
Thr Pro Ser Gly Thr Ser Ser Val Glu Thr Gln Met Arg His Val Ser
290                 295                 300
Ile Ser Tyr Asp Ile Pro Pro Thr Pro Gly Asn Thr Tyr Gln Ile Pro
305                 310                 315                 320
Arg Thr Phe Pro Glu Gly Thr Leu Gly Gln Thr Ser Lys Leu Asp Thr
                325                 330                 335
Ile Pro Asp Ile Pro Pro Pro Arg Pro Pro Lys Pro His Pro Ala His
                340                 345                 350
Asp Arg Ser Pro Val Glu Thr Cys Ser Ile Pro Arg Thr Ala Ser Asp
                355                 360                 365
Thr Asp Ser Ser Tyr Cys Ile Pro Thr Ala Gly Met Ser Pro Ser Arg
                370                 375                 380
Ser Asn Thr Ile Ser Thr Val Asp Leu Asn Lys Leu Arg Lys Asp Ala
385                 390                 395                 400
Ser Ser Gln Asp Cys Tyr Asp Ile Pro Arg Ala Phe Pro Ser Asp Arg
                405                 410                 415
Ser Ser Ser Leu Glu Gly Phe His Asn His Phe Lys Val Lys Asn Val
                420                 425                 430
Leu Thr Val Gly Ser Val Ser Ser Glu Glu Leu Asp Glu Asn Tyr Val
                435                 440                 445
Pro Met Asn Pro Asn Ser Pro Pro Arg Gln His Ser Ser Ser Phe Thr
                450                 455                 460
Glu Pro Ile Gln Glu Ala Asn Tyr Val Pro Met Thr Pro Gly Thr Phe
465                 470                 475                 480
Asp Phe Ser Ser Phe Gly Met Gln Val Pro Pro Ala His Met Gly
                485                 490                 495
Phe Arg Ser Ser Pro Lys Thr Pro Pro Arg Arg Pro Val Pro Val Ala
                500                 505                 510
```

```
Asp Cys Glu Pro Pro Val Asp Arg Asn Leu Lys Pro Asp Arg Lys
            515                 520                 525

Val Lys Pro Ala Pro Leu Glu Ile Lys Pro Leu Pro Glu Trp Glu Glu
    530                 535                 540

Leu Gln Ala Pro Val Arg Ser Pro Ile Thr Arg Ser Phe Ala Arg Asp
545                 550                 555                 560

Ser Ser Arg Phe Pro Met Ser Pro Arg Pro Asp Ser Val His Ser Thr
                565                 570                 575

Thr Ser Ser Ser Asp Ser His Asp Ser Glu Glu Asn Tyr Val Pro Met
            580                 585                 590

Asn Pro Asn Leu Ser Ser Glu Asp Pro Asn Leu Phe Gly Ser Asn Ser
            595                 600                 605

Leu Asp Gly Gly Ser Ser Pro Met Ile Lys Pro Lys Gly Asp Lys Gln
    610                 615                 620

Val Glu Tyr Leu Asp Leu Asp Leu Asp Ser Gly Lys Ser Thr Pro Pro
625                 630                 635                 640

Arg Lys Gln Lys Ser Ser Gly Ser Gly Ser Ser Val Ala Asp Glu Arg
                645                 650                 655

Val Asp Tyr Val Val Asp Gln Gln Lys Thr Leu Ala Leu Lys Ser
            660                 665                 670

Thr Arg Glu Ala Trp Thr Asp Gly Arg Gln Ser Thr Glu Ser Glu Thr
            675                 680                 685

Pro Ala Lys Ser Val Lys
    690

(2) INFORMATION FOR SEQ ID NO:3:

(i) SEQUENCE CHARACTERISTICS:
        (A) LENGTH: 3416 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 335..2419

(xi) SEQUENCE DESCRIPTION: SEQ ID NO:3:

CTCACCGCTG GTGGTGTGGT ACCGGATCGA ATTCGGCACG AGGACCGCTG CCTAGGCGGC          60

GGGACGGCGC GCCTGGCGGC CAGGAGGGCG CACTGAAAGA AGGTCGGCGA GCCCTGGTCC         120

CCGCGGTTCC CGATCGAGTT CCTCTTCAGT CCGCGAATCT GCGGGAGAGG TTCGATCGCC         180

GACACAGGGC GCGGGGAGCC GGGCCGCCCC GTCGGGGGAA TCTGAGACGT CCTCTGGGCT         240

GCGTTTGACC GCCGTGCCCG CCGTGCACGG AGCGCGTCCA CTGTGTCCAC CGACCCCTTT         300

GGTGTCTGGT CCTCGAGTCC TCACGGCGTG CACC ATG AGC GGC GGC GAA GTG            352
                                      Met Ser Gly Gly Glu Val
                                          695             700

GTT TGC TCG GGA TGG CTC CGC AAG TCG CCC CCG GAG AAG AAG TTG AAG          400
Val Cys Ser Gly Trp Leu Arg Lys Ser Pro Pro Glu Lys Lys Leu Lys
            705                 710                 715

CGT TAT GCG TGG AAG AGA AGG TGG TTT GTG TTG CGC AGT GGC CGT TTG          448
Arg Tyr Ala Trp Lys Arg Arg Trp Phe Val Leu Arg Ser Gly Arg Leu
        720                 725                 730

ACT GGA GAC CCG GAT GTC CTG GAG TAT TAC AAA AAC GAT CAT GCC AAG          496
Thr Gly Asp Pro Asp Val Leu Glu Tyr Tyr Lys Asn Asp His Ala Lys
    735                 740                 745

AAG CCT ATT CGG ATT ATT GAT TTA AAT TTA TGT CAG CAA GTT GAT GCT          544
```

-continued

```
                    Lys Pro Ile Arg Ile Ile Asp Leu Asn Leu Cys Gln Gln Val Asp Ala
                        750                 755                 760

GGG TTG ACA TTC AAC AAA AAG GAG TTT GAA AAC AGC TAT ATC TTT GAT              592
Gly Leu Thr Phe Asn Lys Lys Glu Phe Glu Asn Ser Tyr Ile Phe Asp
765                 770                 775                 780

ATC AAC ACC ATC GAC CGG ATT TTC TAC TTG GTG GCA GAT AGT GAG GAA              640
Ile Asn Thr Ile Asp Arg Ile Phe Tyr Leu Val Ala Asp Ser Glu Glu
                785                 790                 795

GAC ATG AAC AAG TGG GTC CGT TGT ATC TGT GAC ATC TGT GGA TTC AAT              688
Asp Met Asn Lys Trp Val Arg Cys Ile Cys Asp Ile Cys Gly Phe Asn
                800                 805                 810

CCC ACA GAA GAA GAT CCT GTG AAG CCG CTG ACT GGC TCC TCA CAA GCA              736
Pro Thr Glu Glu Asp Pro Val Lys Pro Leu Thr Gly Ser Ser Gln Ala
                815                 820                 825

CCC GTC GAT TCA CCT TTC GCT ATA AGT ACA GCA CCA GCC TCC AGT CAG              784
Pro Val Asp Ser Pro Phe Ala Ile Ser Thr Ala Pro Ala Ser Ser Gln
                830                 835                 840

ATG GAA GCT TCT TCA GTC GCG CTA CCT CCT CCT TAC CAG GTC ATC AGC              832
Met Glu Ala Ser Ser Val Ala Leu Pro Pro Pro Tyr Gln Val Ile Ser
845                 850                 855                 860

CTT CCG CCA CAC CCA GAC ACC CTC GGC CTC CAG GAC GAT CCA CAA GAC              880
Leu Pro Pro His Pro Asp Thr Leu Gly Leu Gln Asp Asp Pro Gln Asp
                865                 870                 875

TAC CTC TTG CTG ATC AAC TGT CAA AGC AAG AAG CCT GAA CCT AAC AGA              928
Tyr Leu Leu Leu Ile Asn Cys Gln Ser Lys Lys Pro Glu Pro Asn Arg
                880                 885                 890

ACC CTC TTT GAC TCT GCC AAG CCC ACC TTT TCT GAG ACA GAC TGC AAT              976
Thr Leu Phe Asp Ser Ala Lys Pro Thr Phe Ser Glu Thr Asp Cys Asn
                895                 900                 905

GAC GAC GTC CCT TCC CAC CAG ACT CCT GCT TCC TCC CAG AGC AAA CAC             1024
Asp Asp Val Pro Ser His Gln Thr Pro Ala Ser Ser Gln Ser Lys His
                910                 915                 920

GGA ATG AAT GGC TTT TTC CAG CAA CAA ATG ATG TAT GAC TGC CCA CCG             1072
Gly Met Asn Gly Phe Phe Gln Gln Gln Met Met Tyr Asp Cys Pro Pro
925                 930                 935                 940

TGC CGG CTG ACA TCT GTC TCG GGA GAG TCC AGC CTC TAT AAC CTG CCC             1120
Cys Arg Leu Thr Ser Val Ser Gly Glu Ser Ser Leu Tyr Asn Leu Pro
                945                 950                 955

AGG AGC TAT TCC CAT GAC GTG TTG CCA AAG GAA TCC CCA TCA AGC ACG             1168
Arg Ser Tyr Ser His Asp Val Leu Pro Lys Glu Ser Pro Ser Ser Thr
                960                 965                 970

GAG GCC GAC GGG GAG CTG TAC ACC TTT AAC ACC CCA TCT GGG ACT GCA             1216
Glu Ala Asp Gly Glu Leu Tyr Thr Phe Asn Thr Pro Ser Gly Thr Ala
                975                 980                 985

GGT GTA GAG ACG CAG ATG AGA CAT GTA TCC ATC AGT TTC GAC ATT CCG             1264
Gly Val Glu Thr Gln Met Arg His Val Ser Ile Ser Phe Asp Ile Pro
                990                 995                 1000

CCA ACA CCT GGC AAC ACT TAC CAG ATC CCA CGG ACA TTT CCA GAG AGC             1312
Pro Thr Pro Gly Asn Thr Tyr Gln Ile Pro Arg Thr Phe Pro Glu Ser
1005                1010                1015                1020

ACA CTG GGA CAG TCA TCA AAG CTG GAC ACC ATT CCT GAT ATC CCC CCA             1360
Thr Leu Gly Gln Ser Ser Lys Leu Asp Thr Ile Pro Asp Ile Pro Pro
                1025                1030                1035

CCT CGG CCA CCA AAG CCA CAT CCA ACT CAT GAC CGG TCT CCT GTG GAA             1408
Pro Arg Pro Pro Lys Pro His Pro Thr His Asp Arg Ser Pro Val Glu
                1040                1045                1050

ACG TGT GGA GTC CCA CGC ACG GCC TCG GAC ACT GAC AGC AGT TAC TGT             1456
Thr Cys Gly Val Pro Arg Thr Ala Ser Asp Thr Asp Ser Ser Tyr Cys
                1055                1060                1065

ATC CCT CCT CCA GCA GGC ATG ACG CCC TCC CGG AGT AAT ACC ATT TCC             1504
```

```
Ile Pro Pro Pro Ala Gly Met Thr Pro Ser Arg Ser Asn Thr Ile Ser
    1070                1075                1080

ACC GTG GAT TTG AAC AAG TTG CGG AAA GAT GCT AGT TCT CAA GAT TGC          1552
Thr Val Asp Leu Asn Lys Leu Arg Lys Asp Ala Ser Ser Gln Asp Cys
1085                1090                1095                1100

TAT GAT ATT CCA CGG ACC TTT CCG AGC GAT AGA TCT AGT TGC CTG GAA          1600
Tyr Asp Ile Pro Arg Thr Phe Pro Ser Asp Arg Ser Ser Cys Leu Glu
            1105                1110                1115

GGC TTC CAT AGC CAG TAT AAA ATC AAA AGC GTG TTG ACA GCG GGA GGT          1648
Gly Phe His Ser Gln Tyr Lys Ile Lys Ser Val Leu Thr Ala Gly Gly
        1120                1125                1130

GTC TCG GGT GAA GAG CTG GAT GAG AAC TAC GTT CCC ATG AAC CCC AAC          1696
Val Ser Gly Glu Glu Leu Asp Glu Asn Tyr Val Pro Met Asn Pro Asn
    1135                1140                1145

TCG CCA CCT CGA CAA CAT TCC GGC AGC TTT ACC GAG CCA ATC CAG GAG          1744
Ser Pro Pro Arg Gln His Ser Gly Ser Phe Thr Glu Pro Ile Gln Glu
1150                1155                1160

CCA AAC TAT GTG CCA ATG ACC CCA GGG ACC TTT GAC TTT TCT TCC TTT          1792
Pro Asn Tyr Val Pro Met Thr Pro Gly Thr Phe Asp Phe Ser Ser Phe
1165                1170                1175                1180

GGA ATG CAA GTC CCT CCT CCT GCT CAT ATG GGC TTC AGG TCC AGC CCA          1840
Gly Met Gln Val Pro Pro Pro Ala His Met Gly Phe Arg Ser Ser Pro
            1185                1190                1195

AAG ACC CCT CCC AGG AGG CCA GTT CCT GTT GCT GAC TGT GAA CCA CCC          1888
Lys Thr Pro Pro Arg Arg Pro Val Pro Val Ala Asp Cys Glu Pro Pro
        1200                1205                1210

CCG GTG GAT AGG AAC CTC AAG CCA GAC AGA AAA GTC AAG CCG GCA CCT          1936
Pro Val Asp Arg Asn Leu Lys Pro Asp Arg Lys Val Lys Pro Ala Pro
    1215                1220                1225

TTA GAC ATA AAA CCT CTG TCA GAA TGG GAA GAG CTG CAA GCC CCA GTC          1984
Leu Asp Ile Lys Pro Leu Ser Glu Trp Glu Glu Leu Gln Ala Pro Val
1230                1235                1240

AGA TCT CCC ATC ACC AGG AGC TTC GCT CGG GAC TCC TCT AGG TTT CCC          2032
Arg Ser Pro Ile Thr Arg Ser Phe Ala Arg Asp Ser Ser Arg Phe Pro
1245                1250                1255                1260

ATG TCC CCT CGG CCT GAT TCT GTG CAC AGT ACG ACA TCG AGC AGC GAC          2080
Met Ser Pro Arg Pro Asp Ser Val His Ser Thr Thr Ser Ser Ser Asp
            1265                1270                1275

TCT CAT GAC AGT GAA GAG AAC TAT GTC CCC ATG AAT CCA AAT CTG TCT          2128
Ser His Asp Ser Glu Glu Asn Tyr Val Pro Met Asn Pro Asn Leu Ser
        1280                1285                1290

GGC GAA GAC CCG AAT CTC TTT GCC AGC AAC AGC CTT GAT GGG GGA AGC          2176
Gly Glu Asp Pro Asn Leu Phe Ala Ser Asn Ser Leu Asp Gly Gly Ser
    1295                1300                1305

AGC CCG ATG AAT AAA CCC AAA GGA GAC AAA CAA GTC GAA TAC CTG GAT          2224
Ser Pro Met Asn Lys Pro Lys Gly Asp Lys Gln Val Glu Tyr Leu Asp
1310                1315                1320

TTA GAC CTA GAT TCT GGG AAG TCC ACG CCA CCA CGG AAG CAA AAG AGC          2272
Leu Asp Leu Asp Ser Gly Lys Ser Thr Pro Pro Arg Lys Gln Lys Ser
1325                1330                1335                1340

AGT GGT TCT GGC AGC AGC ATG GCA GAC GAG AGG GTG GAT TAC GTT GTG          2320
Ser Gly Ser Gly Ser Ser Met Ala Asp Glu Arg Val Asp Tyr Val Val
            1345                1350                1355

GTG GAC CAA CAG AAG ACT CTG GCC CTG AAG AGT ACC AGA GAA GCT TGG          2368
Val Asp Gln Gln Lys Thr Leu Ala Leu Lys Ser Thr Arg Glu Ala Trp
        1360                1365                1370

ACG GAT GGG AGG CAG TCC ACA GAG TCC GAG ACA CCC ACC AAG AAT GTG          2416
Thr Asp Gly Arg Gln Ser Thr Glu Ser Glu Thr Pro Thr Lys Asn Val
    1375                1380                1385

AAG TGAAGACATG CCGTCGCCTC TGCCGGCAGA CGAGATCTGA GTTGGAAAGA               2469
```

-continued

```
Lys

GAGATGGCCA AGTGAAGATG TTCCCACTCT CAGTGGGAGC CTCGAGCCAG CAGGGGCAGA      2529

GAGGAAGGAT CTCTCACACA TGTTCAAGCA AATTTAGGTT GTGAATTGGT GCTGTGTGGT      2589

ATTGGATTTA TAACGTGTAA ATAACCCGGG GAAATAGTGT TTTTAGTTCA CAGAGAAGCT      2649

TCTGTCCCTA ATTAACACAC CTGTAGTATT ACTATACTGA TGCACTTTTC ATTTAAAACC      2709

TTGGTTTGGG TCTTCCCGAT CTACCTTAAC AGACTTTCCT TGGGAGGTCT TTTGGCCTCC      2769

TCACACTACT CTATATAACA ATACTAAGTG ACTGAGCTAC TTGTAATTCT GGAAATTCCA      2829

GTTGAAGCTA CAGGGCTAAC ACCATTAAAA CGAGAAGTGA AGTTGACACA TTCGCTTTTC      2889

TCTTGAAGGT GGTAGCCATT AGCTTAAGCT GTAGAACATA GTTGGACTTG TCCTTCGTTG      2949

TTTTCCCAAA AATTCCGGGG ATATTGTATA TAGCAGGTCA AGACCTAGCT CTCTGACTCA      3009

TGTACACTTA GGTTTTAACT GTAGGACTTT GTTATTAATA TTTTTTTTGT TAATGACAGT      3069

GTTGGGTTCA TCGTGTGAAG GTTCTGCTGG GTAGGATCTT GCACCTTTCA AAGACTGCCT      3129

CTTAGTTACA CTAGTAAGCC CCCGAATCAT CCACAGCATG GACTGCTGGC CTGCTCTTAC      3189

TCCTGTTTAT GTGTTAAACA TTATCTGCGA AAGGCAGATT ATACGACTGA CCGATCAGGT      3249

ACGTACAAGG CACTGATGTG CTAATACAGT GATTGGGTCA GACAAAGTGC TTCAGTTAGT      3309

GTGCGTTCGT CCTAATCTTG GTTTAGAATT AATGAAACAG TTGGCGTTCA CTGTCAGCAG      3369

CATAGTGTGA TTTTGAATGA ATTAGGCAGG AATTCAAGAT TACTACT                    3416
```

(2) INFORMATION FOR SEQ ID NO:4:

(i) SEQUENCE CHARACTERISTICS:
        (A) LENGTH: 695 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Gly Gly Glu Val Val Cys Ser Gly Trp Leu Arg Lys Ser Pro
 1               5                  10                  15

Pro Glu Lys Lys Leu Lys Arg Tyr Ala Trp Lys Arg Trp Phe Val
                20                  25                  30

Leu Arg Ser Gly Arg Leu Thr Gly Asp Pro Asp Val Leu Glu Tyr Tyr
            35                  40                  45

Lys Asn Asp His Ala Lys Lys Pro Ile Arg Ile Ile Asp Leu Asn Leu
        50                  55                  60

Cys Gln Gln Val Asp Ala Gly Leu Thr Phe Asn Lys Lys Glu Phe Glu
 65                  70                  75                  80

Asn Ser Tyr Ile Phe Asp Ile Asn Thr Ile Asp Arg Ile Phe Tyr Leu
                85                  90                  95

Val Ala Asp Ser Glu Glu Asp Met Asn Lys Trp Val Arg Cys Ile Cys
            100                 105                 110

Asp Ile Cys Gly Phe Asn Pro Thr Glu Glu Asp Pro Val Lys Pro Leu
        115                 120                 125

Thr Gly Ser Ser Gln Ala Pro Val Asp Ser Pro Phe Ala Ile Ser Thr
    130                 135                 140

Ala Pro Ala Ser Ser Gln Met Glu Ala Ser Ser Val Ala Leu Pro Pro
145                 150                 155                 160

Pro Tyr Gln Val Ile Ser Leu Pro Pro His Pro Asp Thr Leu Gly Leu
                165                 170                 175

Gln Asp Asp Pro Gln Asp Tyr Leu Leu Leu Ile Asn Cys Gln Ser Lys
```

-continued

```
                180                 185                 190
Lys Pro Glu Pro Asn Arg Thr Leu Phe Asp Ser Ala Lys Pro Thr Phe
        195                 200                 205
Ser Glu Thr Asp Cys Asn Asp Val Pro Ser His Gln Thr Pro Ala
    210                 215                 220
Ser Ser Gln Ser Lys His Gly Met Asn Gly Phe Phe Gln Gln Gln Met
225                 230                 235                 240
Met Tyr Asp Cys Pro Pro Cys Arg Leu Thr Ser Val Ser Gly Glu Ser
                245                 250                 255
Ser Leu Tyr Asn Leu Pro Arg Ser Tyr Ser His Asp Val Leu Pro Lys
            260                 265                 270
Glu Ser Pro Ser Ser Thr Glu Ala Asp Gly Glu Leu Tyr Thr Phe Asn
        275                 280                 285
Thr Pro Ser Gly Thr Ala Gly Val Glu Thr Gln Met Arg His Val Ser
    290                 295                 300
Ile Ser Phe Asp Ile Pro Pro Thr Pro Gly Asn Thr Tyr Gln Ile Pro
305                 310                 315                 320
Arg Thr Phe Pro Glu Ser Thr Leu Gly Gln Ser Ser Lys Leu Asp Thr
                325                 330                 335
Ile Pro Asp Ile Pro Pro Arg Pro Pro Lys Pro His Pro Thr His
            340                 345                 350
Asp Arg Ser Pro Val Glu Thr Cys Gly Val Pro Arg Thr Ala Ser Asp
        355                 360                 365
Thr Asp Ser Ser Tyr Cys Ile Pro Pro Ala Gly Met Thr Pro Ser
    370                 375                 380
Arg Ser Asn Thr Ile Ser Thr Val Asp Leu Asn Lys Leu Arg Lys Asp
385                 390                 395                 400
Ala Ser Ser Gln Asp Cys Tyr Asp Ile Pro Arg Thr Phe Pro Ser Asp
                405                 410                 415
Arg Ser Ser Cys Leu Glu Gly Phe His Ser Gln Tyr Lys Ile Lys Ser
            420                 425                 430
Val Leu Thr Ala Gly Gly Val Ser Gly Glu Glu Leu Asp Glu Asn Tyr
        435                 440                 445
Val Pro Met Asn Pro Asn Ser Pro Pro Arg Gln His Ser Gly Ser Phe
    450                 455                 460
Thr Glu Pro Ile Gln Glu Pro Asn Tyr Val Pro Met Thr Pro Gly Thr
465                 470                 475                 480
Phe Asp Phe Ser Ser Phe Gly Met Gln Val Pro Pro Ala His Met
                485                 490                 495
Gly Phe Arg Ser Ser Pro Lys Thr Pro Pro Arg Arg Pro Val Pro Val
            500                 505                 510
Ala Asp Cys Glu Pro Pro Val Asp Arg Asn Leu Lys Pro Asp Arg
        515                 520                 525
Lys Val Lys Pro Ala Pro Leu Asp Ile Lys Pro Leu Ser Glu Trp Glu
    530                 535                 540
Glu Leu Gln Ala Pro Val Arg Ser Pro Ile Thr Arg Ser Phe Ala Arg
545                 550                 555                 560
Asp Ser Ser Arg Phe Pro Met Ser Pro Arg Pro Asp Ser Val His Ser
                565                 570                 575
Thr Thr Ser Ser Ser Asp Ser His Asp Ser Glu Glu Asn Tyr Val Pro
            580                 585                 590
Met Asn Pro Asn Leu Ser Gly Glu Asp Pro Asn Leu Phe Ala Ser Asn
        595                 600                 605
```

```
Ser Leu Asp Gly Gly Ser Ser Pro Met Asn Lys Pro Lys Gly Asp Lys
    610             615             620

Gln Val Glu Tyr Leu Asp Leu Asp Leu Asp Ser Gly Lys Ser Thr Pro
625             630             635                     640

Pro Arg Lys Gln Lys Ser Ser Gly Ser Gly Ser Ser Met Ala Asp Glu
            645             650             655

Arg Val Asp Tyr Val Val Val Asp Gln Gln Lys Thr Leu Ala Leu Lys
            660             665             670

Ser Thr Arg Glu Ala Trp Thr Asp Gly Arg Gln Ser Thr Glu Ser Glu
        675             680             685

Thr Pro Thr Lys Asn Val Lys
690             695
```